United States Patent
Fisher et al.

(10) Patent No.: US 8,097,283 B2
(45) Date of Patent: Jan. 17, 2012

(54) METHODS AND COMPOSITIONS FOR IMAGING

(75) Inventors: Edward A. Fisher, Scarsdale, NY (US); Zahi A. Fayad, New York, NY (US); Kevin J. Williams, Winnewood, PA (US)

(73) Assignee: Mount Sinai School of Medicine, New York, NY (US)

( * ) Notice: Subject to any disclaimer, the term of this patent is extended or adjusted under 35 U.S.C. 154(b) by 1267 days.

(21) Appl. No.: 10/557,094

(22) PCT Filed: Jan. 14, 2005

(86) PCT No.: PCT/US2005/001172
§ 371 (c)(1),
(2), (4) Date: Feb. 16, 2007

(87) PCT Pub. No.: WO2005/070400
PCT Pub. Date: Aug. 4, 2005

(65) Prior Publication Data
US 2007/0243136 A1    Oct. 18, 2007

Related U.S. Application Data

(60) Provisional application No. 60/536,759, filed on Jan. 15, 2004.

(51) Int. Cl.
*A61K 9/16* (2006.01)
(52) U.S. Cl. .................................... 424/498
(58) Field of Classification Search .......... None
See application file for complete search history.

(56) References Cited

U.S. PATENT DOCUMENTS

| 5,582,981 A | 12/1996 | Toole et al. |
| 5,840,867 A | 11/1998 | Toole et al. |
| 6,028,066 A | 2/2000 | Unger |
| 6,498,946 B1 | 12/2002 | Foo et al. |
| 6,541,973 B1 | 4/2003 | Danby et al. |
| 6,580,936 B2 | 6/2003 | Muraki et al. |

(Continued)

FOREIGN PATENT DOCUMENTS

WO    WO-85/04329    10/1985

(Continued)

OTHER PUBLICATIONS

Fires et al, "Recombinant HDL-like Nanoparticles: A Specific Contrast Agent for MRI of Atherosclerotic Plaques", J. Am. Chem. Soc., 2004, 126(50), pp. 16316-163617.*

(Continued)

*Primary Examiner* — Carlos Azpuru
(74) *Attorney, Agent, or Firm* — Marshall, Gerstein & Borun LLP

(57) ABSTRACT

The present invention is directed to synthetic nanoparticles useful as imaging agents for use in MRI, CT, Gamma-scintigraphy, or optical imaging techniques. The synthetic nanoparticles comprise at least one apolipoprotein that is not an apoB lipoprotein, at least one amphipathic lipid, and at least one metallic or non-metallic contrast agent linked through a chelator to a component of the nanoparticle, wherein the one metallic or non-metallic contrast agent is present in an amount of between 5% to about 50% (w/w) of the nanoparticle, and the nanoparticle has a diameter of from about 5 nm to about 50 nm. Compositions and kits comprising the synthetic nanoparticles and methods of making and using the same are also provided.

58 Claims, 5 Drawing Sheets

U.S. PATENT DOCUMENTS

| | | | |
|---|---|---|---|
| 6,586,933 | B1 | 7/2003 | Hardy et al. |
| 6,590,391 | B1 | 7/2003 | Shudo et al. |
| 6,591,128 | B1 | 7/2003 | Wu et al. |
| 6,600,401 | B2 | 7/2003 | Zuk et al. |
| 6,611,143 | B2 | 8/2003 | Kuhara |
| 2002/0168358 | A1 | 11/2002 | Gladue et al. |

FOREIGN PATENT DOCUMENTS

| | | |
|---|---|---|
| WO | WO-88/09345 | 12/1988 |

OTHER PUBLICATIONS

Kreuter et al, "apolipoprotein—mediated transport of nanoparticle-bound drugs across the blood-brain barrier", Jpournal of Drug targeting, 2002, vol. 10(4), pp. 317-325.*

Skajaa et al, "High Density Lipoprotein-Based Contrast AAgents for Multimodal Imaging of Atherosclerosis", Arterisosclerosis, Thrombosis and Vascular Biology. 2010; 30: 169-176, published befor eprint Oct. 8, 2009.*

Corbin et al, "Low Density Lipoprotein Nanoparticles as Magnetic resonance Imaging Contrast Agents", Neoplasia, Jun. 2006, 8(6): 488-496.*

Counsell et al., Lipoproteins as potential site-specific delivery systems for diagnostic and therapeutic agents. *J. Med. Chem.* 25(10): 1115-20 (1982).

Lees et al., 99M technetium-labeled low density lipoprotein: Receptor recognition and intracellular sequestration of radiolabel. *J. Lipid Res.* 32(1): 1-8 (1991).

Moerlein et al., Metabolic imaging with gallium-68- and indium-111-labeled low-density lipoprotein. *J. Nucl. Med.* 32(2): 300-7 (1991).

Shaish et al., Imaging of aortic atherosclerotic lesions by (125)I-LDL, (125)I-oxidized-LDL, (125)I-HDL and (125)I-BSA. *Pathobiol. J. lmmunopathol. Molec. Cell Biol.* 69(4): 225-9 (2001).

Virgolini et al., Binding o f111In-labeled HDL to platelets from normolipemic volunteers and patients with heterozygous familial hypercholesterolemia. *Arterioscler. Thromb.* 12(7): 849-61 (1992).

Virolini et al., Indium-111-labeled low-density lipoprotein binds with high affinity to the human liver as compared to iodine-123 low-density-labeled lipoprotein. *J. NucL Med.* 32(11): 2132-8 (1991).

Supplementary European Search Report, European Patent Application No. 05 70 5684, mailed Jun. 15, 2010.

Ahrens et al., Proc. Natl. Acad. Sci. USA, 95:8443-8448 (1998).
Aikawa et al., Circulation, 97:2433-2444 (1998).
Aikawa et al., Circulation, 100:1215-1222 (1999).
Akiyama et al., Mol. Cell. Biol., 22(8):2607-2619 (2002).
Babaev et al., J. Biol. Chem., 275(34):26293-26299 (2000).
Badimon et al., Circulation, 99:1780-1787 (1999).
Banchereau et al., Nature, 392:245-252 (1998).
Bared et al., Mol. Biol. Cell, 15:5399-5407 (2004).
Basu et al., Proc. Natl. Acad. Sci. USA, 73(9):3178-3182 (1976).
Botnar et al., Circulation, 102:2582-2587 (2000).
Bottcher et al., J. Lipid Res., 41:905-915 (2000).
Braschi et al., J. Lipid Res., 40:522-532 (1999).
Cai et al., Circulation, 106:1368-1373 (2002).
Chawla et al., Nat. Med., 7(1):48-52 (2001).
Chen et al., Circulation, 105:2766-2771 (2002).
Choudhury et al., Arterioscler. Thromb. Vasc. Biol., 22:1065-1074 (2002).
Choudhury et al., Arterioscler. Thromb. Vasc. Biol., 24:1904-1909 (2004).
Corti et al., Circulation, 104:249-252 (2001).
Corti et al., Circulation, 106:2884-2887 (2002).
Coulden et al., Heart, 83:188-191 (2000).
de Vrueh et al., Antimicrob. Agents Chemother., 44(3):477-483 (2000).
Dieu et al., J. Exp. Med., 188(2):373-386 (1998).
Fatterpekar et al., AJNR Am. J. Neuroradiol., 23:1313-1321 (2002).
Fayad et al., Circ. Res., 89:305-316 (2001).
Fayad et al., Circulation, 98:1541-1547 (1998).
Fayad et al., Circulation, 101:2503-2509 (2000).
Fayad et al., Circulation, 102:506-510 (2000).
Fayad et al., Circulation, 106:2026-2034 (2002).
Forte et al., J. Lipid Res., 43:477-485 (2002).
Fuki et al., J. Clin. Invest., 100(6):1611-1622 (1997).
Hatsukami et al., Circulation, 102:959-964 (2000).
Havel et al., J. Clin. Invest., 34:1345-1353 (1955).
Helft et al., Circulation, 105:993-998 (2002).
Jaffer et al., Arterioscler. Thromb. Vasc. Biol., 22:849-854 (2002).
Johnstone et al., Arterioscler. Thromb. Vasc. Biol., 21:1556-1560 (2001).
Jonasson et al., J. Lipid Res., 28:437-445 (1987).
Joseph et al., Nat. Med., 9(2):213-219 (2003).
Kim et al., Circulation, 106:206-299 (2002).
Kunjathoor et al., Arterioscler. Thromb. Vasc. Biol., 22:462-468 (2002).
Lanza et al., Circulation, 106:2842-2847 (2002).
Li et al., J. Clin. Invest., 114(11):1564-1576 (2004).
Li et al., J. Lipid Res., 45:2161-2173 (2004).
Li et al., Radiology, 218:670-678 (2001).
Llodra et al., Proc. Natl. Acad. Sci. USA, 101(32):11779-11784 (2004).
Manjunath et al., J. Clin. Invest., 108(6):871-878 (2001).
Marathe et al., Arterioscler. Thromb. Vasc. Biol., 19:2648-2658 (1999).
Martin-Fontecha et al., J. Exp. Med., 198(4):615-621 (2003).
McConnell et al., Arterioscler. Thromb. Vasc. Biol., 19:1956-1959 (1999).
O'Brien et al., Circulation, 98:519-527 (1998).
O'Brien et al., Circulation, 99:2876-2882 (1999).
Olin-Lewis et al., Circ. Res., 90;1333-1339 (2002).
Pennathur et al., J. Biol. Chem., 279(41):42977-42983 (2004).
Ramsamy et al., J. Biol. Chem., 275(43):33480-33486 (2000).
Randolph et al., Science, 282:480-483 (1998).
Rauch et al., Ann. Intern. Med., 134:224-238 (2001).
Ricote et al., Nature, 391:79-82 (1998).
Ricote et al., Proc. Natl. Acad. Sci. USA, 95:7614-7619 (1998).
Rong et al., Arterioscler. Thromb. Vasc. Biol., 25:122-127 (2005).
Rong et al., Circulation, 104:2447-2452 (2001).
Rong et al., Proc. Natl. Acad. Sci. USA, 100(23):13531-13536 (2003).
Rye et al., Arterioscler. Thromb. Vasc. Biol., 24:421-428 (2004).
Schissel et al., J. Biol. Chem., 273(5):2738-2746 (1998).
Schissel et al., J. Clin. Invest., 98(6):1455-1464 (1996).
Shah et al., Circulation, 103:3047-3050 (2001).
Shamir et al., J. Clin. Invest., 97(7):1696-1704 (1996).
Sloop et al., J. Lipid Res., 28:225-237 (1987).
Sozzani et al., J. Immunol., 161:1083-1086 (1998).
Sparks et al., J. Biol. Chem., 267(36):25839-25847 (1992).
Sparks et al., J. Lipid Res., 33:123-130 (1992).
Suzuki et al., Jpn. J. Pharmacol., 84:113-123 (2000).
Tabas et al., J. Biol. Chem., 268(27):20419-20432 (1993).
Tall et al., J. Biol. Chem., 252(13):4701-4711 (1977).
Tall et al., J. Biol. Chem., 256(4):2035-2044 (1981).
Tall et al., J. Clin. Invest., 110(7):899-904 (2002).
Thuahnai et al., J. Biol. Chem., 279(13):12448-12455 (2004).
Torzewski et al., Arterioscler. Thromb. Vasc. Biol., 18:1386-1392 (1998).
Torzewski et al., Arterioscler. Thromb. Vasc. Biol., 20:2094-2099 (2000).
Torzewski et al., Arterioscler. Thromb. Vasc. Biol., 24:2307-2312 (2004).
Trogan et al., Arterioscler. Thromb. Vasc. Biol., 24:1714-1719 (2004).
Trogan et al., Proc. Natl. Acad. Sci. USA, 99(4):2234-2239 (2002).
Vessby et al., J. Lipid Res., 28:629-641 (1987).
Wang et al., Proc. Natl. Acad. Sci. USA, 101(26):9774-9779 (2004).
Ward et al., Circulation, 102:1186-1191 (2000).
Wasserman et al., Radiology, 223(2):566-573 (2002).
Welch et al., Proc. Natl. Acad. Sci. USA, 100(11):6712-6717 (2003).
Williams et al., Arterioscler. Thromb. Vasc. Biol., 20:1033-1039 (2000).
Worthley et al., Circulation, 101:2956-2961 (2000).
Worthley et al., Circulation, 101:586-589 (2000).

Yancey et al., Arterioscler. Thromb. Vasc. Biol., 23:712-719 (2003).
Yla-Herttuala et al., Proc. Natl. Acad. Sci. USA, 88:10143-10147 (1991).
Yu et al., J. Lipid Res., 45:889-899 (2004).
Yuan et al., Circulation, 98:2666-2671 (1998).
Yuan et al., Radiology, 221(2):285-299 (2001).
Aime et al., J. Magn. Reson. Imaging, 16:394-406 (2002).
Ambrose et al., J. Am. Coll. Cardiol., 12(1):56-62 (1988).
Angeli et al., Immunity, 21:561-574 (2004).
Aoki et al., J. Magn. Reson. Imaging, 9:420-427 (1999).
Aoki et al., Radiology, 194:477-481 (1995).
Breslow, Science, 272:685-688 (1996).
Castrillo et al., Annu. Rev. Cell Dev. Biol., 20:455-480 (2004).
Castrillo et al., Mol. Cell, 12:805-816 (2003).
Chawla et al., Mol. Cell, 7:161-171 (2001).
Chereshnev et al., J. Surg. Res., 111:171-176 (2003).
Choudhury et al., Atherosclerosis, 162:315-321 (2002).
Choudhury et al., J. Cardiovasc. Risk, 9:263-270 (2002).
Choudhury et al., J. Magn. Reson. Imaging, 17:184-189 (2003).
Clay et al., Atherosclerosis, 157:23-29 (2001).
Corti et al., J. Am. Coll. Cardiol., 39(8):1366-1373 (2002).
Falk et al., Circulation, 92:657-671 (1995) (http://circ.ahajournals.org/cgi/content/full/92/3/657).
Fayad, Neuroimag. Clin. N. Am., 12:461-471 (2002).
Fayad et al., Neuroimag. Clin. N. Am., 12:351-364 (2002).
Forster et al., Cell, 99:23-33 (1999).
Fossheim et al., Magn. Reson. Imaging, 17:83-89 (1999).
Fuster et al., Lancet, 353(Suppl II):5-9 (1999) (http://www.thelancet.com/newlancet/any/supplements/vol353s2/body.article2.html).
Glagov et al., N. Engl. J. Med., 316(22):1371-1375 (1987).
Glogard et al., Int. J. Pharm., 233:131-140 (2002).
Grant et al., Magn. Reson. Med., 11:236-243 (1989).
Herfst et al., Arch. Dermatol. Res., 263:325-334 (1978).
Helft et al., J. Am. Coll. Cardiol., 37(4):1149-1154 (2001).
Holmes et al., Am. Heart J., 106:981-988 (1983).
Itskovich et al., Magn. Reson. Med., 49:381-385 (2003).
Johnson et al., Magn. Reson. Q., 9(1):1-30 (1993).
Jonas, Methods Enzymol., 128:553-582 (1986).
Kabalka et al., Magn. Reson. Med., 8:89-95 (1988).
Kaneko et al., Circulation, 94(8):Supp.I-346 (1996).
Kennedy et al., Circulation, 66(Supp III):III-16-III-23 (1982).
Lauffer, Magn. Reson. Q., 6(2):65-84 (1990).
Leesnitzer et al., Biochemistry, 41:6640-6650 (2002).
Lin et al., J. Magn. Reson. Imaging, 7:183-190 (1997).
Lindner, Am. J. Cardiol., 90(Suppl):32L-35L (2002).
Linton et al., Int. J. Obes., 27:S35-S40 (2003).
Little et al., Circulation, 78:1157-1166 (1988).
Lund-Katz et al., Biochemistry, 25:1562-1568 (1986).
Madjid et al., Am. J. Cardiol., 90(Suppl):36L-39L (2002).

Nissen et al., JAMA, 290(17):2292-2300 (2003).
Nunn et al., Q. J. Nucl. Med., 41(2):155-162 (1997).
Nunnari et al., Exp. Mol. Pathol., 51:1-8 (1989).
Ohl et al., Immunity, 21:279-288 (2004).
Ouhlous et al., J. Magn. Reson. Imaging, 15:344-351 (2002).
Pelzer et al., Biochem. Biophys. Res. Commun., 329:726-732 (2005).
Phillips, Adv. Drug Deliv. Rev., 37:13-32 (1999).
Randolph et al., Immunity, 11:753-761 (1999).
Reis et al., J. Vasc. Surg., 34:541-547 (2001).
Rensen et al., Adv. Drug Deliv. Rev., 47:251-276 (2001).
Sahin et al., Curr. Opin. Immunol., 9:709-716 (1997).
Saijo et al., Atherosclerosis, 158:289-295 (2001).
Sallusto et al., Eur. J. Immunol., 28:2760-2769 (1998).
Serruys et al., N. Engl. J. Med., 344(15):1117-1124 (2001).
Skinner et al., Nat. Med., 1(1):69-73 (1995).
Slinkin et al., Bioconjug. Chem., 2:342-348 (1991).
Stary et al., Circulation, 92:1355-1374 (1995) (http://circ.ahajournals.org/cgi/content/full/92/5/1355).
Tamat et al., Pigment Cell Res., 2:281-285 (1989).
Tape et al., Biochim. Biphys. Acta, 1043:295-300 (1990).
Tobias et al., J. Lipid Res., 46:404-411 (2005).
Tontonoz et al., Cell, 93:241-252 (1998).
Torchilin, Adv. Drug Deliv. Rev., 54:235-252 (2002).
Toussaint et al., Circulation, 94:932-938 (1996) (http://circ.ahajournals.org/cgi/content/full/94/5/932).
Tsimikas, Am. J. Cardiol., 90(Suppl):22L-27L (2002).
Van den Eynde et al., Curr. Opin. Immunol., 9:684-693 (1997).
Weiss et al., J. Magn. Reson. Imaging, 14:698-704 (2001).
Weissleder, Nat. Rev. Cancer, 2:1-8 (2002).
Weisweiler, Clin. Chim. Acta, 169:249-254 (1987).
Williams et al., Arterioscler. Thromb. Vasc. Biol., 15:551-561 (1995) (http://atvb.ahajournals.org/cgi/content/full/15/5/551).
Williams et al., Biochim. Biophys. Acta, 875:183-194 (1986).
Williams et al., Curr. Opin. Lipidol., 9(5):471-474 (1998) (http://gateway.ut.ovid.com/gw1/ovidweb.cgi?T=JS&PAGE=fulltext&D=ovft&AN=00041433-199810000-00012&NEWS=N&CSC=Y&CHANNEL=PubMed).
Worthley et al., Circulation, 102:II-809 (2000).
Yuan et al., J. Magn. Reson. Imaging, 15:62-67 (2002).
Yuan et al., Neuroimaging Clin. N. Am., 12:391-401 (2002).
Skajja et al., "High Density Lipoprotein-Based Contrast Agents for Multimodal Imaging of Atherosclerosis," Arteriosclerosis, Thrombosis and Vascular Biology 30: 169-176, 2010; published before eprint Oct. 8, 2009.
Corbin et al., "Low Density Lipoprotein Nanoparticles as Magnetic Resonance Imaging Agents," Neoplasia 8(6): 488-496, 2006.

* cited by examiner

METHODS AND COMPOSITIONS FOR IMAGING

This invention was made with government support under Grant Numbers HL061814, HL069446, and HL078667 awarded by the National Institutes of Health (NIH). The government has certain rights in the invention.

This application is a U.S. National Phase Application pursuant to 35 U.S.C. 371 of International Application No. PCT/US2005/001172 which was filed Jan. 14, 2005, claiming benefit of priority of U.S. Patent Application No. 60/536,759 filed Jan. 15, 2004. The entire disclosure of each of the foregoing applications is incorporated herein by reference.

FIELD OF THE INVENTION

This invention relates to imaging techniques such as magnetic resonance imaging (MRI) and, more particularly, to a composition for use in such a method wherein the composition comprises a metallic or non-metallic contrast agent conjugated to a component of a high density lipoprotein.

BACKGROUND OF THE INVENTION

Atherosclerosis remains a major health problem in the U.S., with significant morbidity and mortality. Imaging of the arteries allows the clinician to screen, detect and characterize the disease to provide useful, anatomical information which has been utilized to guide decisions about treatment and to enable the delivery of therapy in the case of percutaneous interventions (Holmes et al., Am Heart J. 1983; 106:981-8; Kennedy et al., Circulation. 1982; 66:III16-23; Serruys et al., N Engl J Med. 2001; 344:1117-24). However, x-ray angiography is an invasive procedure, and it images only the vessel lumen and hence the silhouette of the subset of lesions that impinge upon the lumen. Atherosclerosis can develop in the arterial wall and be accommodated by outward (or positive) arterial remodeling (Glagov et al., *N Engl J Med*. 1987; 316: 1371-5; Ward et al., *Circulation*. 2000; 102:1186-91). The importance of this phenomenon has been highlighted in angiographic studies demonstrating that non-severe stenoses are more often associated with acute coronary events than are severe coronary stenoses (Ambrose et al., J Am Coll Cardiol. 1988; 12:56-62; Little et al., Circulation. 1988; 78:1157-66). From a pathological perspective, plaques with large lipid cores and thin fibrous caps are more prone to rupture, leading to thrombosis and vascular events, than plaques with small, securely contained lipid cores and thick caps (Falk et al., Circulation. 1995; 92:657-71; Fuster et al., Lancet. 1999; 353 Suppl 2:SII5-9).

To date, numerous different techniques have been employed to image characterize and analyze atherosclerotic plaques. Such techniques include angioscopy, thermography, near-infrared spectroscopy, near-infrared photon tomography, optical coherence tomography, Raman spectroscopy, computed tomography, nuclear imaging, and ultrasound techniques (Fayad et al., Circ Res. 2001; 89:305-16; Saijo et al., Atherosclerosis. 2001; 158:289-95; Chen et al., Circulation. 2002; 105:2766-71; Tsimikas et al., Am J Cardiol. 2002; 90:22L-27L; Lindner, Am J Cardiol. 2002; 90:32L-35L; Madjid et al., Am J Cardiol. 2002; 90:36L-39L; Fayad et al., Circulation. 2002; 106:2026-34; Fayad et al., Neuroimaging Clin N Am. 2002; 12:351-64). However magnetic resonance imaging (MRI) has emerged as the preferred technique for atherosclerosis plaque imaging. MRI is a non-invasive, non-destructive, three-dimensional imaging technique that differentiates tissue structure on the basis of proton magnetic resonance properties with a wide range of image contrast (Choudhury et al., J Cardiovasc Risk. 2002; 9:263-70; Choudhury et al., Arterioscler Thromb Vasc Biol. 2002; 22:1065-74). The non-invasive nature of MRI allows virtually unlimited number of repetitive measurements to be made in a single animal, and permits time-based assessment of a given plaque's lesion size and other morphological features (i.e., progression, regression, or compositional changes).

Atherosclerotic lesions from a variety of large animals have previously been examined using MRI systems (e.g., rabbits (Skinner et al., Nature Medicine. 1995; 1:69-73; McConnell et al., Arterioscler Thromb Vasc Biol. 1999; 19:1956-9; Worthley et al., Circulation. 2000; 101:586-9; Worthley et al., Circulation. 2000; 102:II-809; Johnstone et al., Arterioscler Thromb Vasc Biol. 2001; 21:1556-60; Helft et al., J Am Coll Cardiol. 2001; 37:1149-1154; Helft et al., Circulation. 2002; 105:993-8), pigs (Lin et al., J of Magn Reson Imaging. 1997; 7:183-90; Worthley et al., Circulation. 2000; 101:2956-2961; Corti et al., J Am Coll Cardiol. 2002; 39:1366-1373), non-human primates (Kaneko et al., Circulation. 1996; 94:I-346. Abstract), and humans (Toussaint et al., Circulation. 1996; 94:932-8; Yuan et al., Circulation. 1998; 98:2666-71; Coulden et al., Heart. 2000; 83:188-91; Hatsukami et al., Circulation. 2000; 102:959-64; Fayad et al., Circulation. 2000; 101: 2503-2509; Fayad et al., Circulation. 2000; 102:506-510; Botnar et al., Circulation. 2000; 102:2582-7; Corti et al., Circulation. 2001; 104:249-52; Yuan et al., Radiology. 2001; 221:285-99; Yuan et al., Clin N Am. 2002; 12:391-401; Jaffer et al., Arterioscler Thromb Vasc Biol. 2002; 22:849-54; Ouhlous et al., J Magn Reson Imaging. 2002; 15:344-51; Fayad et al., Neuroimaging Clin N Am. 2002; 12:461-71; Kim et al., Circulation. 2002; 106:296-9; Corti et al., Circulation. 2002; 106:2884-7; Cai et al., Circulation. 2002; 106: 1368-73) by use of conventional MR systems (1.5T) with a spatial resolution $\geq 300$ µm. To study small structures, such as the aorta of mice (less ~1 mm in luminal diameter), it is necessary to increase the signal-to-noise ratio by use of high-magnetic field equipped with small radiofrequency (RF) coils. The strong magnetic fields allow the use of MR microscopy (MRM) with in vivo spatial resolution of 25-100 µm (Johnson et al., Magnetic Resonance Quarterly. 1993; 9:1-30; Weissleder, Nature Rev Cancer. 2002; 2:11-8).

Non-contrast enhanced MRM plaque imaging and characterization techniques utilize the inherent differences in "natural" MR relaxation properties of different plaque components. Recent reports show that contrast-enhanced gadolinium-MRI may be useful for atherosclerotic plaque characterization such as differentiation between fibrotic and non-fibrotic plaques, identification of neovasculature, and possible detection of plaque inflammatory status (Aoki et al., Radiology. 1995; 194:477-81; Aoki et al., J Magn Reson Imaging. 1999; 9:420-7; Weiss et al., J. Magn. Reson. Imaging. 2001; 14:698-704; Yuan et al., J Magn Reson Imaging. 2002; 15:62-7; Wasserman et al., Radiology. 2002; 223:566-73). The gadolinium (Gd) contrast agents, routinely used in clinical MRI, alter the MR proton relaxation of the imaged tissue. The chelated Gd does not penetrate phospholipid cellular membranes because of its highly hydrophilic properties (Merbach et al., The chemistry of contrast agents in medical magnetic resonance imaging. Chischester: John Wiley & Sons; 2001). It stays entirely confined into the extracellular space after intravenous administration, does not bind plasma proteins and it is eliminated unmetabolized by the kidneys (Niendorf et al., Safety and risk of Gadolinium-DTPA: extended clinical experience after more than 20 million applications. Berlin: Blackwell Wissenschafts-Verlag GmbH;

1996). This non-specific enhancement to the plaque and/or plaque components may facilitate the imaging and the characterization of mouse lesions.

However, in order to achieve good resolution of the MR image, a certain quantity of the imaging agent must accumulate at the site of interest being examined. Preferably, the imaging agent should specifically accumulate at the site being examined. For example, the required tissue concentration of an MR contrast agent is ~$10^{-4}$-$10^{-6}$ Molar (Nunn et al., Q J Nucl Med. 1997; 41:155-62; Aime et al., J Magn Reson Imaging. 2002; 16:394-406). For radionuclide imaging it is only ~$10^{-10}$ Molar. This is a great challenge since the molecular epitopes expressed at $10^{-9}$ or $10^{-12}$ molar concentrations must be detected. Another challenge is to get the imaging agent to and into the site of interest. One way to reach the required local concentration of an MR contrast agent is to use nanoparticulate carriers, such as micelles, emulsions, or liposomes, which carry the imaging agent to the site of interest. However, the size of these liposomes and emulsions is such that it exceeds the size required to readily permeate into the extracellular space and hence into a plaque (Sloop et al., J Lipid Res. 1987; 28:225-37). For example, liposomes typically have a diameter of about 100-400 nm and cannot enter a plaque unless the endothelium is damaged (e.g., Lanza et al., Circulation. 2002; 106:2842-7; Li et al., Radiology. 2001; 218:670-8). Therefore, delivery of imaging agents through the use of such nanoparticles is practically restricted to either targets on the endothelium or in lesions in which endothelial integrity has been breached, for example, as after balloon angioplasty (Lanza et al., Circulation. 2002; 106:2842-7).

Reconstituted lipoproteins have previously been used as delivery vehicles for lipophilic drugs. Lipoproteins are produced mainly by the intestine and liver (or by processing of intestine or liver-derived lipoproteins) and are the native transporters in the circulation of a variety of lipophilic and hydrophilic compounds and are classified into 4 main categories depending on size and composition (i.e., in order of decreasing diameter: chylomicrons, very low density lipoproteins (VLDL), low density lipoproteins (LDL) and high density lipoproteins (HDL) (Havel et al., The Metabolic and Molecular Bases of Inherited Disease. New York: McGraw-Hill; 2001:2705-2716). With the exception of HDLs, the lipoproteins also suffer the same drawbacks as micelles, conventional emulsions and liposomes, in that the entities are too large to serve as good vehicles for the delivery of imaging agents.

LDLs are particularly unsuitable for such delivery because, in addition to being larger than the optimal size (on average LDLs are larger than 20 nm), the major protein constituent of LDLs is apoB, a very large and hydrophobic protein, which makes it difficult to reconstitute LDL (rLDL) particles. Further, LDL moieties are spontaneously retained in atherosclerotic lesions (Williams et al., Arterioscler Thromb Vasc Biol. 1995; 15:551-61), thereby making it difficult to selectively detect specific molecular targets of interest within the plaque. Yet another factor that makes LDLs unattractive as delivery vehicles is that LDL is an atherogenic particle, and so it is difficult to justify the possible risks from administration of rLDL to patients already at high risk for cardiovascular disease.

Micelles, much like LDLs, also do not serve well as delivery vehicles to enter atherosclerotic plaques, because they are spontaneously retained for prolonged periods of time, rendering them unsuitable for the selective detection of specific molecules of interest.

Hence, there is a need for a delivery vehicle reconstituted that is small enough to freely enter an atherosclerotic plaque and that is not readily trapped unless specifically modified and provides sufficient quantities of an imaging agent for use in MRI or MR spectroscopy or other imaging techniques such as CT, gamma-scintigraphy, and optical, positron emission tomography (PET), and combined imaging techniques.

SUMMARY OF THE INVENTION

The present invention provides various nanoparticles that are used for the delivery of an imaging contrast agent. The compositions of the present invention include, but are not limited to, a synthetic nanoparticle, the synthetic nanoparticle comprising at least one apolipoprotein that is not an apoB lipoprotein, at least one amphipathic lipid, and at least one metallic or non-metallic contrast agent linked through a chelator to a component of the nanoparticle, the one metallic or non-metallic contrast agent being present in an amount of between 5% to about 50% (w/w) of the nanoparticle, and the synthetic nanoparticle having a diameter of from about 5 nm to about 50 nm. It is contemplated that greater amounts of contrast agent e.g., up to 100% (w/w) of the component of the nanoparticle to which the contrast agent is bonded may be presented. Further, while the size of the nanoparticles is preferably between 5 nm and 25 nm, the diameter may be up to 50 nm. The nanoparticles may be spherical, discoidal or a distorted disc shape, e.g., ellipsoidal.

In preferred embodiments, the apolipoprotein is an amphipathic apolipoprotein or a fragment thereof. The metallic contrast agent may preferably be selected from the group consisting of Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), and Er(III), Indium (In), Technetium (Tc), and Barium. In addition, the metallic contrast agents could include crystals and other particulate materials (oxides, quantum dots, etc.) The non-metallic contrast agent may preferably be selected from the group consisting of iodine (I), Bromine, Fluorescein, Carboxyfluorescien, Calcein, $F^{18}$, $Xe^{133}$, $I^{125}$, $I^{131}$, $I^{123}$, $P^{32}$, $Tl^{201}$, $K^{42}$, $In^{111}$, $Fe^{59}$, $Tc^{99}$, $Cr^{51}$, $Ga^{67}$, $Cu^{64}$, $Rb^{82}$, $C^{11}$, $N^{13}$, $O^{15}$, $Mo^{99}$, $Kr^{81}$, and $Dy^{165}$. In specific embodiments, the metallic contrast agent is gadolinium. In particularly preferred embodiments, the metallic or non-metallic contrast agent is conjugated to a lipid component of the synthetic nanoparticle. Such a lipid component of the synthetic nanoparticle may selected from the group consisting of a sterol, a phospholipid, a sterol ester, a diacylglycerol and a triacylglycerol. In certain embodiments, the sterol of the imaging agent is cholesterol. In other embodiments, the sterol ester is cholesteryl ester.

In preferred embodiments, the metallic or non-metallic contrast agent is associated with a phospholipid and preferably, selected from the group consisting of phosphatidylcholine (PC), phosphatidylethanolamine (PE), phosphatidylserine (PS), phosphatidylinositol (PI), phosphatidylglycerol (PG), cardiolipin (CL), a sphinolipid, sphingomyelin (SM), and phosphatidic acid (PA). In particularly preferred embodiments, the phospholipid is PC. The PC (or indeed any other phospholipids) may comprise any fatty acid of e.g., between 4 and 24 carbon chains in length. The two fatty acids of the phospholipids may be the same or they may be different. In preferred embodiments, the PC is POPC. In yet other preferred embodiments, the phospholipid is PE. In specific embodiments, the phospholipid is dimyristoyl-PE (DMPE). In still other preferred embodiments, the phospholipid is a modified PE. Preferably, the modified PE is poly-lysine PE. In still other embodiments, the poly-lysine PE is poly-lysine dimyristoyl-PE.

It is contemplated that the metallic or non-metallic contrast agent may alternatively be conjugated to a protein component of the synthetic nanoparticle. Such a protein may be selected from the group consisting of an apolipoprotein A-I, A-II, A-IV, C-I, C-II, C-III and E.

In preferred embodiments, the synthetic nanoparticle in the imaging agent comprises a phospholipid:steryl ester:sterol: TAG:ApoAI ratio (w/w) of 100:62:25:11:2. In specific embodiments, the imaging agent comprises between 1 and 50 metallic or non-metallic contrast agent molecules per synthetic nanoparticle. In various aspects of the invention, the metallic or non-metallic contrast agent molecule is conjugated to a phospholipid moiety and the phospholipid moiety accommodates more than one metallic or non-metallic agent molecule. In more specific aspects, the imaging agent comprises 10 metallic or non-metallic contrast agent molecules per synthetic nanoparticle. In other aspects, the imaging agent is defined as comprising between about 5 mg and about 30 mg of apolipoprotein. The imaging agent of the invention may comprise between about 80 and about 90 phospholipids per synthetic nanoparticle. Other embodiments define the imaging agent as comprising about 2 apolipoprotein molecules per synthetic nanoparticle. In still further embodiments, the synthetic nanoparticle comprises about 1 apolipoprotein molecule to about every 40 phospholipid molecules.

The imaging agents of the invention may further comprise a targeting moiety to facilitate targeting of the agent to a specific site in vivo. The targeting moiety may be any moiety that is conventionally used to target an agent to a given in vivo site and may include but is not limited to, an antibody, a receptor, a ligand, a peptidomimetic agent, an aptamer, a polysaccharide, a drug and a product of phage display. In particular embodiments, the targeting moiety may be conjugated to a detectable label.

Preferably, the diameter or the longest dimension of the nanoparticle is between about 5 nm to about 18 nm. The diameter may be between about 5 to about 12 nm. In particularly preferred embodiments, the diameter is less than 10 nm.

The imaging agent may be one which comprises two or more different contrast agents. These two or more different contrast agents may all be metallic, all be non-metallic or the imaging agent may comprise some metallic contrast agents and some non-metallic contrast agents. In additional embodiments, the agent may further comprise a drug to be delivered at an in vivo site targeted by the targeting moiety.

Other aspects of the present application describe a pharmaceutical composition comprising an imaging agent as described herein and a pharmaceutically acceptable carrier or diluent.

Also contemplated are methods of in vivo imaging of a site within a subject comprising administering to the subject an imaging agent comprising a metallic or non-metallic contrast agent conjugated to component of a synthetic nanoparticle. Preferably, the imaging agent used in such a method comprises a targeting moiety that specifically targets the imaging agent to the in vivo site. In specific embodiments, the in vivo site being imaged is the site of an atherosclerotic plaque. In such specific embodiments, the targeting moiety is selected from the group consisting of antibodies against lipoprotein lipase, oxidized epitopes on atherosclerotic plaques oxLDL MDA, antibodies against matrix metalloproteinases and anti-tissue factor antibodies.

In other embodiments, the in vivo site is the site of a tumor and the targeting moiety comprises a moiety that recognizes a tumor-specific binding partner present on the tumor. More particularly, the binding partner is selected from the group consisting of an antibody against a tumor-specific antigen, a receptor for a ligand expressed by the tumor, a ligand for a receptor expressed on the tumor.

In other embodiments the in vivo site is the site of an organ and the targeting moiety comprises a moiety that is exclusively expressed on the organ. In particular embodiments, the in vivo site is the site of platelet deposition in an animal and the targeting moiety comprises a fibronectin or GP IIb/IIIa receptor ligand or a fibrin binding protein.

Further aspects of the invention are directed to methods of making an imaging composition, the method comprising: obtaining a composition comprising a phospholipid optionally covalently linked to a chelating moiety and reacting the composition with a composition comprising a first metallic or non-metallic contrast agent to produce a phospholipid-chelating (optionally) agent-metallic/non-metallic agent conjugate; co-sonicating the conjugate of step (a) with: a predetermined amount of HDL apolipoprotein; a predetermined amount of a mixture of phospholipids mixed in a ratio found in circulating HDL; a predetermined amount of sterol; and a predetermined amount of HDL core lipids comprising triglycerides (TAG) and cholesteryl ester in a ratio found in circulating HDL; for a time period sufficient to allow the conjugate and the individual components of nanoparticle to coalesce into nanoparticulate structures; and isolating structures that have a size of between about 5 to about 12 nm diameter. In preferred embodiments, the first metallic contrast agent is selected from the group consisting of Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), Er(III), Indium (In), Technetium (Tc), and Barium. The first non-metallic contrast agent is selected from the group consisting of Iodine (I), Bromine, Fluorescein, Carboxyfluorescien, and Calcein.

The methods of the making the compositions may further comprise providing a second phospholipid-chelating agent-metallic or non-metallic contrast agent, wherein the second contrast agent is different from the first contrast agent. In exemplary embodiments, one of the contrast agents may be a metallic agent whereas the second contrast agent is a non-metallic agent. In those embodiments that employ a chelating agent, the chelating agent preferably is selected from the group consisting of DTPA, EDTA, BOPTA, DOTA, DO3A and aDO3A. In preferred embodiments, the sterol component is selected from the group consisting of cholesterol, stigmasterol, ergosterol, lanosterol, and sitosterol. In other preferred embodiments, the phospholipid in the phospholipid-chelating agent-metallic (or non-metallic) contrast agent conjugate is selected from the group consisting of consisting of PC, PE, PS, PI, PG, CL, SM and PA. Preferably, the phospholipid mixture is a mixture of two or more phospholipids selected from the group consisting of consisting of PC, PE, PS, PI, PG, CL, SM and PA.

The phospholipids, core lipids, sterol, and apolipoprotein are preferably mixed in a phospholipids:steryl ester:sterol: TAG:Apolipoprotein ratio (w/w) of 100:62:25:11:2. In preferred embodiments, the method produces reconstituted synthetic nanoparticle particles that comprise between about 80 and about 90 phospholipids per synthetic nanoparticle. Preferably, the method produces nanoparticle that comprise about 1 apolipoprotein molecule to about every 40 phospholipid molecules. The methods are used to produce synthetic nanoparticle that comprise between 1 and 30 metallic contrast ions per synthetic nanoparticle. In specific embodiments, the phospholipid covalently linked to a chelating moiety is a modified phospholipid that can accommodate more than one metallic or non-metallic contrast agent. Preferably, the modified phospholipid is a poly-L-lysine-PE. Still more preferably, the poly-L-lysine-PE is dimyristoyl-poly-L-lysine. In preferred aspects the method further comprises obtaining a composition comprising a biotinylated phospholipid reacting the composition with a composition comprising a targeting agent to produce a phospholipid-targeting agent conjugate, and providing the phospholipid-targeting agent conjugate in the co-sonicating mixture.

Also contemplated herein are diagnostic kits comprising a metallic or non-metallic contrast agent conjugated to component of a high density lipoprotein (HDL) in a pharmaceutically acceptable carrier or diluent; and a device for delivering the composition to a subject prior to diagnostic imaging of the subject. Other kits contemplated herein are kits for producing an imaging agent the kit comprising a first composition comprising a metallic or non-metallic contrast agent; a second composition comprising a phospholipid covalently linked to a chelating moiety; a third composition comprising HDL apoproteins; and a fourth composition comprising free phospholipid. In addition, the kits may comprise instructions for reconstituting HDL. Preferred metallic agents for the first composition include but are not limited to, Gd(III), Mn(II), Mn(III), Cr(II), Cr(III), Cu(II), Fe (III), Pr(III), Nd(II) Sm(III), Tb(III), Yt(III) Dy(III), Ho(III), Eu(III), and Er(III), Indium (In), Technetium (Tc), and Barium. In addition, the metallic contrast agents include crystals and other particulate materials (oxides, quantum dots, etc.). Preferred non-metallic agents for the first composition include but are not limited to Iodine (I), Bromine, Fluorescein, Carboxyfluorescien, Calcein. $F^{18}$, $Xe^{133}$, $I^{125}$, $I^{131}$, $I^{123}$, $P^{32}$, $Tl^{201}$, $K^{42}$, $In^{111}$, $Fe^{59}$, $Tc^{99}$, $Cr^{51}$, $Ga^{67}$, $Cu^{64}$, $Rb^{82}$, $C^{11}$, $N^{13}$, $O^{15}$, $Mo^{99}$, $Kr^{81}$, and $Dy^{165}$.

Any contrast agent that is employed in MRI, CT, Gamma-scintigraphy, or optical imaging techniques may be used in the present invention. The kits may further comprise a fifth composition comprising sterol, such as e.g., cholesterol, stigmasterol, ergosterol, lanosterol, and sitosterol. The kits may further comprise a sixth composition comprising a HDL core lipids. In particular aspects, the fourth composition comprising the phospholipid comprises either individually or as a mixture one or more phospholipids selected from the group consisting of consisting of PC, PE, PS, PI, PG, CL, SM and PA. In certain embodiments, the phospholipids is covalently linked to a chelating moiety such as e.g., DTPA, EDTA, BOPTA, DOTA, DO3A and aDO3A.

Preferably, the second phospholipid composition is a poly-L-lysine-PE. More particularly, poly-L-lysine-PE is poly-L-lysine-DMPE. As used herein the "core lipids" are those lipids that form the core of the nanoparticle. Preferably, the core lipids comprise cholesteryl ester and/or TAG.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

DETAILED DESCRIPTION OF THE PREFERRED EMBODIMENTS

Figure 1:
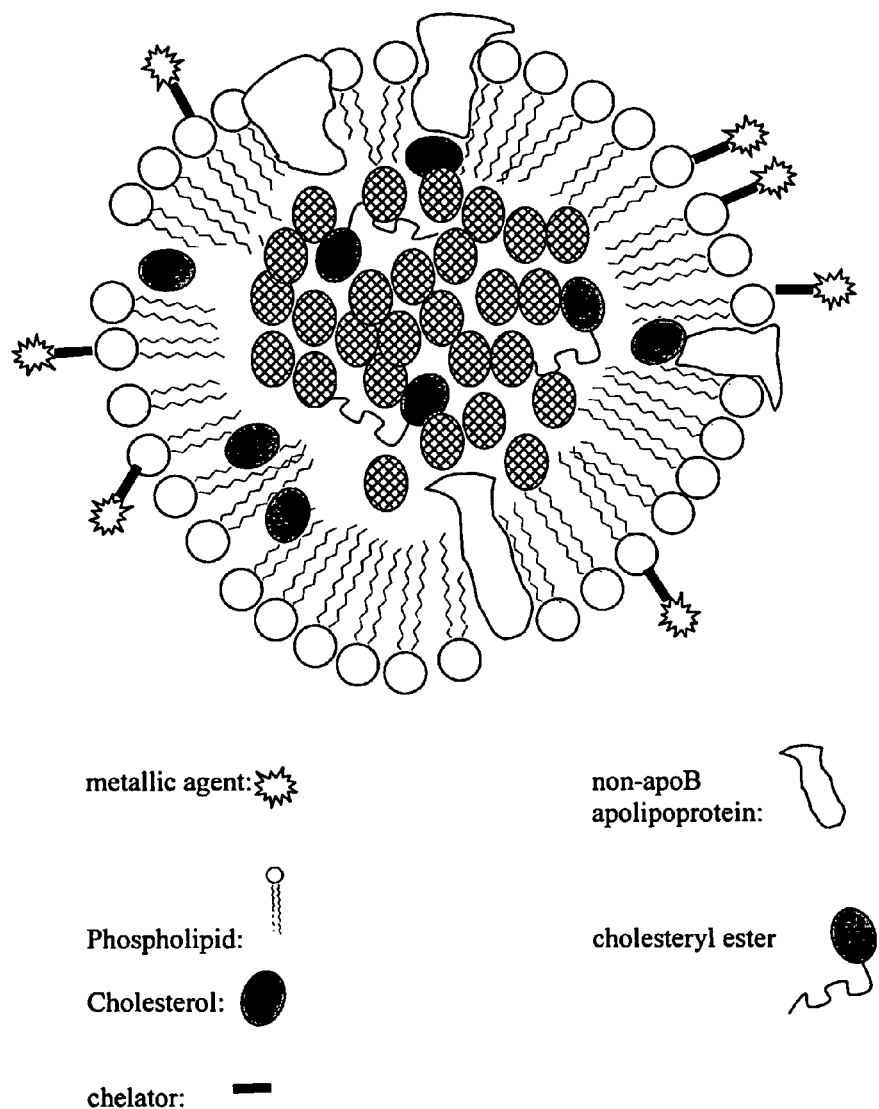
FIG. 1 Schematic representation of an imaging agent of the present invention.

Magnetic resonance microscopy (MRM) has been effectively used as a non-invasive method for the quantification of atherosclerosis to documents its progression and regression of atherosclerosis in vivo (Skinner et al., Nature Medicine. 1995; 1:69-73; McConnell et al., Arterioscler Thromb Vasc Biol. 1999; 19:1956-9; Worthley et al., Circulation. 2000; 101:586-9; Worthley et al., Circulation. 2000; 102:II-809; Johnstone et al., Arterioscler Thromb Vasc Biol. 2001; 21:1556-60; Helft et al., J Am Coll Cardiol. 2001; 37:1149-1154; Helft et al., Circulation. 2002; 105:993-8; Lin et al., J of Magn Reson Imaging. 1997; 7:183-90; Worthley et al., Circulation. 2000; 101:2956-2961; Corti et al., J Am Coll Cardiol. 2002; 39:1366-1373.63. Kaneko et al., Circulation. 1996; 94:I-346. Abstract; Toussaint et al., Circulation. 1996; 94:932-8; Yuan et al., Circulation. 1998; 98:2666-71; Coulden et al., Heart. 2000; 83:188-91; Hatsukami et al., Circulation. 2000; 102:959-64; Fayad et al., Circulation. 2000; 101: 2503-2509; Fayad et al., Circulation. 2000; 102:506-510; Botnar et al., Circulation. 2000; 102:2582-7; Corti et al., Circulation. 2001; 104:249-52; Yuan et al., Radiology. 2001; 221:285-99; Yuan et al., Clin N Am. 2002; 12:391-401; Jaffer et al., Arterioscler Thromb Vasc Biol. 2002; 22:849-54; Ouhlous et al., J Magn Reson Imaging. 2002; 15:344-51; Fayad et al., Neuroimaging Clin N Am. 2002; 12:461-71; Kim et al., Circulation. 2002; 106:296-9; Corti et al., Circulation. 2002; 106:2884-7; Cai et al., Circulation. 2002; 106: 1368-73; Johnson et al., Magnetic Resonance Quarterly. 1993; 9:1-30; Weissleder, Nature Rev Cancer. 2002; 2:11-8). However, significant progress is still needed in spatial and temporal resolution of plaque characteristics and in the molecular imaging of plaque components. Such progress will be greatly facilitated by the availability of novel imaging compositions that are small enough to freely enter an atherosclerotic plaque in sufficient quantities to provide an enhanced MR image. These particles should preferably possess the following properties be a) small enough to readily penetrate into the interstitial fluid, b) able to carry large amounts of a contrast agent, c) non-toxic including non-atherogenic, d) poorly retained in diseased tissue without the addition of a targeting agent, e) able to carry large amounts of a targeting agent, and f) easy to manufacture and store.

The present invention addresses this need by providing imaging contrast agents conjugated to component of a reconstituted high density lipoprotein (rHDL). By "rHDL" it should be understood that the present invention contemplates a synthetic molecule that exhibits some of the characteristics and features of plasma-derived HDL moieties (e.g., small diameter, non-atherogenic etc.) but is a synthetic molecule and is not formed from plasma HDL. Commercial sources of HDL include: Biodesign International; Athens Research and Technology; Intracel Corp; Scripps Laboratories; Academy Biomedical Co. Thus, the compositions of the present invention comprise a synthetic, rHDL moiety conjugated to a contrast agent. For the first time it is shown that such synthetic rHDL moieties may be used as delivery vehicles for such imaging agents. The use of synthetic rHDL for imaging in vivo sites is advantageous because of all of the lipoprotein compositions, rHDL is the easiest to reconstitute, and it is sufficiently small (~10 nm diameter) (Rensen et al., Adv Drug Deliv Rev. 2001; 47:251-76) to penetrate readily into the extracellular space (Sloop et al., J Lipid Res. 1987; 28:225-37) and freely enter and exit sites such as the sites of atherosclerotic plaques (Sloop et al., J Lipid Res. 1987; 28:225-37; O'Brien et al., Circulation. 1998; 98:519-27; Kunjathoor et al., Arterioscler Thromb Vasc Biol. 2002; 22:462-8.). In addition, rHDL has the advantage of not being atherogenic and, therefore, will not pose the same cardiovascular risks that might be associated with the use of LDL moieties. Moreover, unlike LDL moieties and micelles, the HDL moieties are not retained at the in vivo site for prolonged periods of time.

The preferred particles of the invention comprise at least one amphipathic protein or peptide and at least one amphipathic lipid, to form a structure that can be spherical or discoidal. To readily penetrate into the interstitial fluid, the particles must be 25 nm or less in diameter, if spherical, or 25 nm or less in their longest dimension, if discoidal. For structural stability, ease of manufacture, and ability to carry significant amounts of contrast and/or targeting agents, the particles should be at least 5 nm in their largest dimension. Furthermore, to carry large amounts of a contrast agent, said agent is incorporated through the inclusion of an amphipathic chelator, that is, a molecule that has a hydrophobic portion that incorporates into the particle, and a chelating portion that binds an MRI contrast agent. To be non-atherogenic, the protein or peptide component must not be an apolipoprotein-B.

The inclusion of an amphipathic protein or peptide aids the structural stability of the particle, particularly when the particle has a discoidal shape. Exemplary proteins or peptides are selected from the group consisting of an HDL apolipoprotein, an apolipoprotein A-I, an apolipoprotein A-II, a protein or peptide that contains an amphipathic alpha-helix, and an amphipathic protein or peptide. Ampipathic proteins that may be used herein are commercially available from e.g., Biodesign International; Athens Research and Technology; Intracel Corp; Scripps Laboratories; Academy Biomedical Co). The inclusion of an amphipathic lipid creates a hydrophobic zone within the particle that allows the incorporation of an amphipathic chelator.

The hydrophobic zone also allows the incorporation of an amphipathic complex that comprises a targeting agent. Said complexes include, but are not limited to, an amphipathic lipid covalently linked to an antibody; and an amphipathic lipid covalently linked to an avidin, which is then non-covalently linked to a biotinylated antibody. Other complexes include poly lysine phospholipids-Gd complexes in which the targeting moity is provided.

Finally, for several reasons, the rHDL particles must be synthetic rather than isolated from human plasma. In particular, the use of naturally occurring lipoproteins isolated from human plasma is not contemplated, rather the rHDL particles described herein are synthetic. The use of synthetic molecules have a number of potential advantages. Firstly, the use of such molecules avoids transmission of blood-borne infectious agents, which are frequently present in conventionally isolated human plasma lipoproteins. Secondly, isolation of large quantities of human plasma lipoproteins is impractical and expensive, because it requires large amounts of human plasma as starting material and then tedious isolation procedures. Thirdly, human plasma lipoproteins vary substantially from batch to batch, depending on the individual donor(s), recent dietary intake, and other factors. Fourthly, synthetic particles allows the skilled artisan to circumvent the problems of oxidized or readily oxidizable lipids, such as highly unsaturated lipids. Oxidized or readily oxidizable lipids can be toxic and can impair stability during storage. As noted elsewhere, the preferred amphipathic lipid is POPC, which is relatively resistant to oxidation and is readily available commercially in pure form. Fifthly, incorporation of large amounts of contrast agents and/or targeting agents into a pre-existing lipoprotein is difficult, if not impossible, without significant disruption of said pre-existing lipoprotein. Exemplary methods of forming the synthetic rHDL compositions of the invention are described in further detail in the examples herein below.

In particularly preferred aspects of the invention the synthetic rHDL is reconstituted with the contrast agent and a second agent that allows the targeting of the imaging composition to a specific site. While some of the discussion herein focuses on atherosclerotic plaques, it should be understood that other sites in the body also may be targeted with the compositions of the invention. These compositions of the invention are able to locate to a specific target site and produce a desirable result of a large increase in signal intensity from plaque retention of the synthetic rHDL because of the presence of a specific targeting molecule of interest. This is of particular interest because it has previously been noted that, for example, in atherosclerotic plaques HDL is very inefficiently retained in the plaque site. Although it may be possible to increase the retention of HDL moiety by increasing the relative amount of apoE or C-reactive protein present in the HDL, it is contemplated that the presence of the targeting moiety is advantageous because it facilitates the controlled retention of the imaging agent at the site of interest, thereby promoting an increase in the signal at that site as compared to use of the metallic contrast agent alone.

As described herein it was unexpectedly found that the MRI contrast compositions can be formulated as conjugates of a component of a synthetic rHDL composition. These metal imaging agents are useful in all areas of diagnostics that can employ MRI imaging of a given tissue or in vivo site. In exemplary embodiments, the compositions of the present invention are generated by incorporating a paramagnetic metal ion complexed with a chelating agent having a lipophilic moiety, into synthetic rHDL moieties. Preferably, the chelating agent is a polyaminopolycarboxylate chelating agent. Further, it is preferred that there are multiple metal ions complexed per synthetic rHDL entity. The lipophilic paramagnetic chelate that serves as the metallic contrast agent will preferably be conjugated to a phospholipid moiety. As phospholipids are an integral are relatively easily incorporated into synthetic rHDL moieties, and so the metal contrast agent is thus easily incorporated into the synthetic rHDL compositions of the present invention. The entire complex which contains the HDL and the metal contrast agent, and optionally also contains a targeting moiety, is referred to herein as an "imaging agent."

Advantageously, complexing the metallic contrast agent in the manner described herein eliminates or reduces the toxicity and other undesirable side effects of the metallic agent whilst at the same time retaining the paramagnetic properties of the metal ion that confer the imaging action of the paramagnetic ion, i.e., change in relaxivity of the hydrogen atoms of water. As discussed herein below, numerous chelating agents may be used to produce a paramagnetic ion composition that would be suitable for reconstitution in synthetic rHDL compositions herein. However, it is envisioned that polyaminopolycarboxylic acids will be particularly useful for complexing the paramagnetic ions intended for MRI imaging of human or animal body.

Methods and compositions for making and using the imaging agents of the present invention are described in further detail herein below. As described herein it was unexpectedly found that the MRI contrast compositions can be formulated as conjugates of a component of a synthetic rHDL composition. These metal imaging agents are useful in all areas of diagnostics that can employ MRI imaging of a given tissue or in vivo site.

A. Reconstituted HDL

To the extent that the present application is directed to methods and compositions which employ certain lipoproteins, the present section is provided as a discussion of the types of such agents that are to be used in the present invention.

Those of skill in the art are aware of methods and compositions for producing recombinant lipoproteins as vehicles for drug delivery (Rensen et al., *Adv. Drug Del. Rev.* 47:251-276, 2001). As is detailed in Rensen et al., lipoproteins are spherical macromolecular particles made up of a hydrophobic core of triglycerides (TAG) and cholesteryl esters, which are emulsified by a shell of amphipathic phospholipids, unesterified cholesterol, and one or more apolipoproteins. The unesterified sterol and the apolipoproteins in the outer layer of the lipoproteins stabilize the overall structure. These naturally occurring structures circulate in vivo and are intrinsically involved in lipid transport. These structures are ideal candidates for drug delivery because being endogenous, these agents are less likely to promote an immune response, and they readily evade detection and elimination through the reticuloendothelial system.

Lipoprotein classes are distinguishable from each other based on their density in ultracentrifugations. There are four major classes of lipoproteins circulating in human blood, and they differ from each other with respect to size, lipid composition and apolipoprotein composition. The four entities are chylomicrons, VLDLs, LDLs, and HDLs. The characteristics of these entities are described in Table 1 of Rensen et al., 2001 and reproduced in the following Table:

TABLE 1

Physical properties and composition of plasma lipoprotein classes

| | Chylomicron | VLDL | LDL | HDL |
|---|---|---|---|---|
| Density (g/ml) | <0.96 | 0.96-1.006 | 1.019-1.063 | 1.063-1.21 |
| Diameter (nm) | 75-1200 | 30-80 | 19-25 | 5-12 |
| Mobility on agarose | Origin | pre-β | β | α |
| Composition (% w/w) | | | | |
| Triglycerides | 80-95 | 45-65 | 4-8 | 2-7 |
| Phospholipid | 3-6 | 15-20 | 18-24 | 26-32 |
| Cholesteryl ester | 2-4 | 6-10 | 45-50 | 15-20 |
| Cholesterol | 1-3 | 4-8 | 6-8 | 3-5 |
| Protein | 1-2 | 6-10 | 18-22 | 45-55 |

TABLE 1-continued

Physical properties and composition of plasma lipoprotein classes

| | Chylomicron | VLDL | LDL | HDL |
|---|---|---|---|---|
| Apolipo-proteins | A-I, II, IV B48 C-I, II, III E | — B100 C-I, II, III E | — B100 — — | A-I, II, IV — C-I, II, III E |

In the methods of the present invention, the lipoproteins of interest are synthetic reconstituted HDLs. HDL is also known to contain apolipoproteins D and J (Bottcher A. et al. *J. Lipid Res.* 41:905-915, 2000). It is therefore contemplated that the synthetic reconstituted HDLs of the present application also may contain apolipoproteins D and J. These lipoproteins are characterized by a density of about 1.063 g/ml to about 1.21 g/ml, and as such, are the densest of the four classes of lipoproteins. However, the diameter of these lipoproteins is the smallest of the lipoprotein classes and varies between 5 to 12 nm. In preferred embodiments of the present invention the synthetic rHDL compositions have an average diameter of between about 5 nm and about 15 nm. A particularly preferred range is a range of between 5-10 nm. It is envisioned that in any imaging composition of the present invention may contain a range of sizes of synthetic rHDL, but the average size of the particles will be in the above range. Thus, the compositions may have particles that range have diameters of between 5-15 nm, other exemplary ranges of diameters in a given composition are between 5-10 nm, 5-8 nm, 5-6 nm. In preferred embodiments the average diameter size of the synthetic rHDLs is about 10 nm, alternatively, the average diameter is about 6 nm, 7 nm, 8 nm, 9 nm, 10 nm, 11 nm, 12 nm, 13 nm, 14 nm or 15 nm. The average size of the synthetic rHDLs may be as large as 18 nm. Preferably, the above recited average sizes are those sizes that are achieved when the synthetic rHDL has been reconstituted with at the least the metallic contrast agent.

In those embodiments, in which the imaging composition comprises both a metallic (or non-metallic) agent and a targeting agent, it is preferred that the average diameter of the synthetic rHDL moiety comprised of the synthetic rHDL, metallic agent (or non-metallic) and targeting moiety does not exceed 18 nm.

Schematically, the rHDLs of the present invention are depicted in FIG. 1. In that figure, the metallic contrast agent (1) is linked through a polyaminopolycarboxylate chelating agent (2) that comprises a hydrophobic group to the phosphate-linked headgroup of a phospholipid moiety (3) in the rHDL. Of course, it should be understood that this is a preferred embodiment, and those of skill in the art may produce synthetic rHDLs in which the metallic or non-metallic contrast agent is covalently linked to, or otherwise associated with, another component of the synthetic rHDL, such as for example, the apolipoprotein component (4), or the sterol component (5). In particular embodiments, it may be desirable to have the metallic or non-metallic contrast agent sequestered in the core of the synthetic rHDL. For such embodiments, the metallic contrast agent (1) may be linked through a polyaminopolycarboxylate chelating agent (2) to a fatty acyl residue of the TAG (6) or even the fatty acyl residue of the cholesteryl ester, or another hydrophobic molecule.

The synthetic rHDL compositions of the present invention in which the paramagnetic metal ion is bonded to a chelator that is attached to the phosphate-linked headgroup of a phospholipid has shown strikingly high contrast efficiency in MRI imaging, particularly of atheroscleorotic plaques. This is due to the fact that HDL moieties are able to effectively and efficiently locate to such plaques. Such location to the plaques is further enhanced by the presence of targeting moieties such as e.g., an antibody, or other specific binding partner of a moiety that is present at the site being imaged. Indeed, under certain conditions, endogenous HDL particles have been reported to be present in atherosclerotic vessels (for example, Pennathur S et al. J Biol Chem 279:42977, 8 Oct. 2004). These HDL particles, however, are abnormal and are likely to be pro-inflammatory. Thus, regardless of whatever extent that they might localize to plaques, they are unsuitable for use as vehicles for delivery of contrast agents, drugs, or other substances in humans. In contrast to naturally occurring HDL particles, the recombinant HDL-like nanoparticles (rHDL) of the current invention allow localization to plaques and other target areas, without necessarily promoting pro-inflammatory effects.

It is contemplated that the compositions of the present invention produce a contrast effect at least 20% better than the contrast seen when the metallic ion is presented alone or in phospholipid, micellar, or LDL forms of delivery. More preferably, the compositions produce a 30%, 35%, 40%, 45%, 50%, 55%, 60%, 70% 75% or higher percentage better contrast, than that of comparative compositions of the prior art in which these other forms of delivery vehicles are used. Without being bound by particular theory or mechanism, the compositions of the present invention are more effective contrast agents than those available in the art because they have the advantage of having a particle sizes between 5 and 25 nm, thus being small enough to integrate into the site being imaged. Further, the agents of the present invention also optionally may comprise targeting agents that facilitate a increased affinity for the imaged site such that the imaging agent is retained and accumulated at the site. The preferred agent of the invention preferably has a diameter (if spherical), or longest dimension (if discoidal), of less than 20 nm and greater than 5 nm, more preferably the rHDLs have a diameter or longest dimension of between about 5 nm and about 15 nm.

As discussed above, the metallic agent preferably comprises a chelating moiety that facilitates the conjugation of the metallic agent to for example, the phospholipid moiety. In certain embodiments, it is desirable to have the metallic agent chelating moiety present near the outer surface of the synthetic rHDL hydrophobic portion of a sphingolipid, and/or the two fatty acyl groups of a phosphatidylcholine, phosphatidylethanolamine, or other glycerophospholipid in the inner side of the HDL moeity. The fatty acids of the phospholipids may include, but are not limited to, e.g., saturated and unsaturated $C_1$ to $C_{24}$ fatty acids. The chelating moiety may be an alcohol like methanol, ethanol, propanol, butanol (n-, iso-, tert-), pentanol, hexanol (and isomers), heptanol, octanol (and isomers), nonanol, decanol and fatty alcohols; as aromatic alcohols, one may cite substituted and unsubstituted benzyl- and higher phenylalkyl-alcohols. The chelating molecule may also be provided with the hydrophobic group in form of a carboxylate amide with hydrophobic aliphatic or aromatic amines. Such amines may be saturated and unsaturated $C_1$ to $C_{24}$ amines like methylamine, ethylamine, propylamine, butylamine (n-, iso-, tert-), pentylamine, hexylamine (and isomers), octylamine (and isomers), nonylamine, decylamine, aminoadamantan and fatty amines; as aromatic amines, one may cite substituted and unsubstituted benzyl- and higher phenylalkyl-amines. Alternatively, the polycarboxylic chelating agent can be provided with lipophilic hydrophobic groups linked to the alkylene segments of the molecular back-bone, or to the α-carbon of the carboxylate functions or to a hydroxyl group when present in the chelating agent.

In preferred embodiments, the present invention employs Gd-DTPA as the metallic contrast agent comprising the polyaminopolycarboxylate agent chelating agent. In preferred embodiments the chelating agent is DTPA, however, those of skill in the art are aware that other chelating agents could readily be used in place of DTPA, such other agents include, but are not limited to EDTA, BOPTA, DOTA, DO3A and/or their derivatives. In the imaging agents of the invention, the paramagnetic metal may be any paramagnetic metal traditionally used in MRI techniques and may for example be selected from e.g., Gd(III), Mn(II), Mn(III), Cr(II), Cr(III), Cu(II), Fe (III), Pr(III), Nd(III) Sm(III), Tb(III), Ybt(II) Dy(III), Ho(III), Eu(II), Eu(III), Er(III), Indium (In), Technetium (Tc), and Barium. In other aspects of the invention, non-metallic agents are used as contrast agents. Exemplary, but non-limiting non-metallic contrast agents include Iodine (I), Bromine, Fluorescein, Carboxyfluorescien, and Calcein.

A preferred composition for use in the preparation of the rHDL compositions of the present invention is Gd-DTPA-phosphatidylethanolamine (PE). Those of skill in the art are aware of how to produce and use DTPA-PE as a liposomal MRI contrast agent (Grant et al., Magn. Reson. Med. 11:236-43, 1989). While in preferred embodiments, it is envisioned that the phospholipid is PE, it should be understood that the metallic contrast agent may be conjugated to any phospholipid using techniques such as those that have previously been used to generate DTPA-PE. Such phospholipids include but are not limited to phosphatidic acid (PA), phosphatidylcholine (PC), phosphatidylethanolamine (PE, particularly dimyristoyl-sn-glycero-phosphatidylethanolamine (DMPE)), phosphatidylserine (PS), phosphatidylglycerol (PG), phosphatidylinositol (PI), cardiolipin (CL), sphingomyelin (SM), and other sphingolipids. In addition to being conjugated to a phospholipid, it may be possible to conjugate the metallic agent to e.g., a mono-phosphate ester of a substituted or partially substituted glycerol, at least one functional group of said glycerol being esterified by saturated or unsaturated aliphatic fatty acid, or etherified by saturated or unsaturated alcohol, the other two acidic functions of the phosphoric acid being either free or salified with alkali or earth-alkali metals. Preferably the phosphate esters will include monophosphates of fatty acid glycerides selected from dimyristoylphosphatidic acid, dipalmitoylphosphatidic acid, or distearoylphosphatidic acid. Also, it should be understood that the fatty acyl moieties of the phospholipids may vary in length. For example, it is envisioned that the phospholipids, TAG, cholesteryl esters, and monophosphate esters of the glycerol may comprise fatty acids of between $C_4$ to $C_{24}$ carbons in length. Thus, it should be noted that that the fatty acyl moieties of the phospholipids may be any fatty acyl moiety commonly found in phospholipids. For example, the fatty acyl moieties may comprise between 4 and 24 carbons and may be saturated, or alternatively may comprise one, two, three or more double bonds. Further, the two fatty acid chains of the phospholipids may be the same fatty acid or alternatively, the phospholipid may comprise two different fatty acyl moieties. In particularly, preferred embodiments, the phospholipids contain two myristoyl moieties as in DMPE. However, while DMPE is a preferred phospholipid it is contemplated that DMPC, DMPA, DMPI and the like also may be used.

In preferred embodiments, the phospholipids may also include diacyl and dialkyl glycerophospholipids in which the aliphatic chains have at least twelve carbon atoms.

As can be seen from FIG. 1, in addition to having phospholipid conjugated to the metallic contrast agent, the rHDLs also comprise phospholipids as part of the overall HDL structure. It is contemplated that the rHDL may be made up only of one type of phospholipid or more preferably, the rHDL will be made up of a mixture of phospholipids. Preferably, in the mixture of phospholipids, the ratio of the individual types of phospholipid may be comparable to the ratio of the same phospholipids seen in HDLs circulating in the blood.

In addition to the phospholipid and TAG lipid components of the rHDL, the compositions also comprise sterol esters in the core of the rHDL and sterols interspersed between the phospholipid layer of the rHDL. While in preferred embodiments the sterol moiety of the steryl ester and the sterol in the phospholipid layer is cholesterol, it should be understood that other common sterols, such as ergosterol, stigmasterol, phytosterol, sitosterol, and lanosterol, also may serve as the sterol moiety. Other sterols, whether isolated from natural sources or synthetically generated, also may be used.

The ratios of the various HDL components to each other in the rHDL compositions of the present invention should be guided by the molar w/w ratios given above in Table 1 for HDL moieties. In the compositions containing phospholipids, the weight proportion of the phospholipids:steryl ester: sterol:TAG:ApoAI may vary in a wide range e.g. from $100\pm50\%:62\pm50\%:25\pm50\%:11\pm50\%:2\pm50\%$. Composition will affect particle size (because of the surface-to-core ratio), and can even affect particle shape (discoidal if there is insufficient core lipid). However, those of skill in the art are aware of variations in the ratios of phospholipids (e.g., DMPC and DPPC) mixed with different ratios of apoA-I (Tall et al. J Biol Chem. 252(13):4701-11, 1977.) Compositions such as those described by Tall et al. may be varied by addition of differing quantities of core lipids as was described, for example, in a later study on phospholipid-enrichment of HDL (Tall AR & Green PH, JBC 256:2035-2044, 1981.)

In particularly preferred embodiments, the ratio is 100:62: 25:11:2. Other exemplary ranges may be calculated by reference to Table 1, herein above which provides that the % w/w ratio of the components of various particles. The use of a large excess of chelate may result in unnecessary waste of the chelating/imaging agent while an excess of phospholipid beyond certain concentration does not provide extra benefit. Within these ratios, it is contemplated that the ratio of phospholipid: metallic agent can vary from 75:25 to 0:100, and the ratio of phospholipid:sterol can vary from 5:10 to 20:1. In other embodiments, the rHDL may contain no sterol (i.e., be composed of phospholipids only with no sterol).

It is contemplated that the compositions of the present invention may be produced by lyophilisation of the composition whereby a dry, pulverulent formulation is obtained. This form of the paramagnetic composition is particularly convenient for long term storage. The storage in the powder form is simplified by the fact that reconstitution of the composition be achieved by dispersion of the lyophilised powder in a physiologically acceptable liquid carrier, will form a suspension useful as a blood pool NMR imaging contrast agent. The lyophilisation is a straight forward freeze-drying process requiring no particular precautions or measures. In certain embodiments, it may be desirable to produce HDLs in a lyophilized form and then re-constituted such HDLs using a sonicator or an extruder.

The methods for making compositions according to the invention generally comprise selecting as components a paramagnetic contrast agent with an appropriate polycarboxylic acid chelating agent provided with a suitable lipophilic group in admixture with one or more phospholipids, TAGs, sterols and steryl, particularly cholesteryl, esters and apolipoproteins dispersing the components together so they coalesce into rHDL form. Preferably, the components are dispersed in a physiologically acceptable aqueous liquid carrier such as water or saline, neat or buffered, according to usual practice. Depending upon the choice of components, the dispersion can be achieved by gentle mixing, by detergent dialysis (e.g., cholate dialysis) or by more energetic means such as homogenization, microfluidization, other shear methods, or sonication.

Those of skill in the art are aware of methods for reconstituting HDL moieties (Jonas, Method. Enzymol., 128:553-568, 1986). Such methods include detergent mediated synthesis (see p 561, Jonas Method. Enzymol., 128:553-568, 1986), cosonication of HDL components (Jonas at page 565), or through the spontaneous interaction of apolipoproteins with the lipid vesicles. For a detailed discussion of exemplary methods and stoichiometry for the reconstitution of rHDL molecules of the invention, see Example 1.

B. Targeting Moieties

As noted herein throughout, a major advantage of using rHDL is that while it can freely enter and exit lesions, its steady-state levels in plaques should be relatively low, unless deliberate steps are made to promote its retention. Ideally, this retention should be dependent on specific molecules of interest, resulting in an obvious increase in signal intensity (relative to the low background). Thus, in specific embodiments, Gd-rHDL particles are constructed that incorporate specific surface components to cause these particles to be retained in atherosclerotic plaques. Such surface components may be any component that facilitates targeting of the HDL to a given site. In preferred embodiments, the targeting moiety is an antibody.

By "antibody" the present invention intends to encompass antibody fragments and derivatives, thus the term includes, but is not limited to, polyclonal, monoclonal, chimeric, single chain, Fab fragments and fragments produced by a Fab expression library. Such fragments include fragments of whole antibodies which retain their binding activity for an antigen or other marker expressed at the site that is to be targeted by the rHDL compositions of the invention. Such fragments include Fv, F(ab') and F(ab')2 fragments, as well as single chain antibodies (scFv), fusion proteins and other synthetic proteins which comprise the antigen-binding site of the antibody. While the antibodies are principally being used herein as targeting agents, such antibodies and fragments thereof may also be neutralizing antibodies, i.e., those which inhibit biological activity of the polypeptides which they recognize, and therefore may serve the additional purpose of rendering the rHDL compositions as being useful as diagnostics and therapeutics. In exemplary embodiments, in the rHDL compositions of the invention Fab or other antibody fragments discussed above can be conjugated to avidin then complexed to biotinylated PE as described in e.g., Example 2.

In preferred embodiments, the choice of antibody will be directed by knowledge of plaque biology, which provides a reasonable set of candidates for plaques in general and at different stages of development. For general plaque markers, antibodies against lipoprotein lipase (Williams et al., *Arterioscler Thromb Vasc Biol.* 1995; 15:551-61; Jonasson et al., J Lipid Res. 1987; 28:437-45; Yla-Herttuala et al., Proc Natl Acad Sci USA. 1991; 88:10143-7; Babaev et al., J Biol Chem. 2000; 275:26293-9), oxidized epitopes (O'Brien et al., Circulation. 1999; 99:2876-82), including oxLDL MDA (Herfst et al., Arch Dermatol Res. 1978; 263:325-4) are suitable. For markers of unstable plaques, antibodies against matrix metalloproteinases (Aikawa et al., Circulation. 1998; 97:2433-

44) and tissue factor may be used (Rong et al., Circulation. 2001; 104:2447-52; Aikawa et al., Circulation. 1999; 100:1215-22; Badimon et al., Circulation. 1999; 99:1780-7; Rauch et al., Ann Intern Med. 2001; 134:224-238). The antibodies for these plaque components are either commercially available and known to those of skill in the art and have previously used a number of them in studies of mouse atherosclerosis (e.g., Rong et al., Circulation. 2001; 104:2447-52). Also, contemplated for use herein are antibodies or other agents that bind matrix components. Such agents include apoE and C-reactive protein, as well as antibodies against biglycan, chondroitin sulfate, and versican. (see, for example, Olin-Lewis et al., Circ Res. 90(12):1333-9, 2002). In certain embodiments, oxidation specific antibodies are used. Those of skill in the art are referred to Torzewski et al. which provides a teaching in the art of Oxidized antibodies to malondialdehyde and uses thereof in imaging plaques and plaque stabilization (Torzewski et al., Arterioscler. Thromb Vasc Biol. 2004; 24:2307-2312).

For each incorporated antibody, the final rHDL particles should be tested as above (size, surface charge, penetration of interstitial fluid, biodistribution and relaxivity) and the results compared to native and rHDL-Gd-DPTA-PE particles before testing as a plaque imaging agent by undergoing the series of in vivo and ex vivo studies described below.

Other markers that will be used as targeting agents include arterial-wall sphingomyelinase, a key factor that promotes lipoprotein retention and aggregation (Williams et al., Arterioscler Thromb Vasc Biol. 1995; 15:551-61; Tabas et al., J Biol Chem. 1993; 268:20419-32; Schissel et al., J Clin Invest. 1996; 98:1455-64; Schissel et al., J Biol Chem. 1998; 273:2738-46; Williams et al., Curr Opin Lipidol. 1998; 9:471-4; Marathe et al., Arterioscler Thromb Vasc Biol. 1999; 19:2648-58). Sphingomyelinase is abundant in atherosclerotic plaques, and its role in atherogenesis is to digest sphingomyelin in lipoproteins, thereby generating ceramide. Ceramide is a fusogen that causes the lipoproteins to aggregate, forming large complexes that can no longer leave the plaque. There are two conditions required for sphingomyelinase to mediate this process: i) the lipoproteins must have a sufficiently high content of sphingomyelin, to allow efficient digestion by arterial-wall sphingomyelinase (Schissel et al., J Biol Chem. 1998; 273:2738-46); and ii) the particles must initially remain in the lesion long enough to become digested. Thus, certain of the rHDL compositions of the invention comprise both an antibody to promote some initial retention, but also a high sphingomyelin content to promote digestion by sphingomyelinase to increase particle aggregation and trapping in the plaque. Thus, based on a well-characterized pathophysiologic process, sphingomyelin containing rHDL compositions of the invention will amplify the signal from antibody-mediated retention of Gd-rHDL in atherosclerotic plaques.

In addition, it is contemplated that the agents of the invention may be targeted to the extracellular matrix components. Illustrative, but not restrictive, examples of extracellular matrix components include, but are not limited to, a proteoglycan, a chondroitin sulfate proteoglycan, a heparan sulfate proteoglycan, a mixed proteoglycan, versican, perlecan, biglycan, decorin, a small leucine-rich proteoglycan, a syndecan, a glypican, betaglycan, macrophage colony-stimulating factor, a collagen, a type I collagen, a type III collagen, an elastin, a fibronectin, a laminin, a non-proteoglycan, a macrophage-derived molecule, a smooth muscle cell-derived molecule, a mast cell-derived molecule, a molecule derived from an inflammatory cell, a molecule derived from a non-inflammatory cell, an endothelial-derived molecule, and a cell-derived matrix component.

Further it has been shown that the apoAI moiety of HDL interacts with ABCA1 and undergoes an intracellular travel route (called retroendocytosis; Bared et al., Mol. Biol. Cell, 15: 5399-5407, 2004). It is contemplated that the proteins encountered during this route would be in close proximity to HDL. As such, the rHDL compositions of the present invention, with or without molecular targeting agents, could be employed to transport materials to intracellular locations within the cell. It is contemplated that macrophage intracellular localization of the Gd can be achieved using the compositions of the present invention, consistent with the retroendocytosis pathway delivery HDL to the interior of the cells. Since HDL interacts with ABCAI, by extension, the HDL may further interact with proteins associated with ABCA1, the rHDL compositions of the invention can those be used to target such intracellular proteins. Other transporters in the ABC family, such as ABCG1 and ABCG4, and SR-BI, all known to interact with HDL, may also serve as "bridges" between the rHDL with imaging (with or without targeting agents) so that the presence of a variety of intracellular molecules may be sensed. Besides assessing the presence of such molecules, the rHDL-imaging agent approach may also be useful to explore cellular pathways—i.e., the sub-cellular localization and transfers of the rHDL would serve as a tracer and could provide direct physical evidence of any process used in the cellular itinerary of rHDL. Proteins that interact with ABCA1 or ABC-family proteins include CFTR, GTPases (Cdc42), apoptosis proteins (FADD, PDZ proteins (Beta2-syntrophin, alpha 1-syntrophin, Lin7), SNARE proteins (syntaxin-13, syntaxin 1A, SNAP-23), phagosome proteins (flotillin-1, syntaxin-13). The rHDL compositions could be used to target the plasma membrane or intracellular locations within endosomes and lysosomes.

Cell surface proteins that may serve as target for the rHDL compositions of the invention can be divided up into 3 groups-receptors, adhesion molecules, and miscellaneous proteins. The proteins should be on the cell surface of the major types of cells found in plaques; i.e., endothelial cells, macrophages, smooth muscle cells, and lymphocytes.

Receptors that can serve as targets in the present invention include, e.g., scavenger receptor, SR-BI, LDLR, LRP, apoE receptor, VLDL receptor, CD36, oxidized LDL receptor, sphingosine-1P receptor, CD44. Of course there are many many other receptors, such as FGF, insulin, EGF, etc—that may also be targeted. Adhesion molecules that may be targeted include e.g., VCAM, ICAM, cadherins, integrins, selectins, and their binding partners (which are also cell-surface molecules). In specific embodiments, it is contemplated that the skilled artisan could prepare rHDL compositions to target T cells for imaging with reagents against CD2 (all T cells) CD3 (all T cells), CD4 (major subset of T cells), CD8 (major subset of T cells),and CD90 (all T cells). Markers for B cells include, e.g., B220 (a B cell-specific isoform of CD45), CD19 and CD20 (both useful pan-targets for both human and mouse B cells). Other useful markers may include NK1.1 that targets NKT cells as well as CD3 (for T cells).

Of course, in addition to antibodies other agents may be used as targeting moieties. Such agents include, but are not limited to ligands for receptors (or vice versa) that are expressed on the surface of a given site to be targeted.

In certain embodiments, the targeting moiety is an aptamer. Aptamers are DNA or RNA molecules that have been selected from random pools based on their ability to bind other molecules. Aptamers have been selected which bind nucleic acid, proteins, small organic compounds, and even entire organisms. Methods and compositions for identifying and making aptamers are known to those of skill in the art and are described e.g., in U.S. Pat. Nos. 5,840,867 and 5,582,981 each incorporated herein by reference. In addition to aptamers, DNA, RNA, or modified DNA or RNA molecules also may be included as targeting moieties.

Further, in addition to targeting of atherosclerotic plaques, it is contemplated that any other disorder may readily be imaged. For example, tumors are known to be associated with various characteristic genes that encode tumor rejection antigen precursors (or TRAPs), which are processed into tumor rejection antigens in tumor cells. Such TRAP-encoding genes would be useful components to target with e.g., antibodies or with other agents that recognize the expression products of these genes. Exemplary TRAP-encoding genes include members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, mutated proto-oncogenes such as p21ras, mutated tumor suppressor genes such as p53, tumor associated viral antigens such as HPV16 E7. See, e.g., review by Van den Eynde and van der Bruggen (1997) in Curr. Opin. Immunol. 9:684-693, Sahin et al. (1997) in Curr. Opin. Immunol. 9:709-716.

Receptors such as e.g., cytokine receptors may specifically be targeted by using a cytokine having a receptor binding domain capable of interacting with a cell receptor site. Such cytokines include but are not limited to IL-1, IL-2, IL-3, IL-4, IL-5, IL-6, IL-7, IL-8, IL-9, IL-10, IL-11, IL-12, IL-13, EPO, G-CSF, M-CSF, GM-CSF, IGF-1, and LIF. It should be understood that these are merely exemplary ligands of certain receptors and the compositions of the invention may readily be adapted to comprise any ligand to any receptor that is expressed on the cell surface, so long as that ligand can be modified to be attached to e.g., a phospholipid moiety of the rHDLs of the present invention and yet retain its receptor binding capability. In addition, C-reactive protein (CRP) and/or to activated complement could also be targeted. Those of skill in the art are referred to Torzewski et al., (Arterioscler. Thromb. Vasc. Biol., Sep. 1, 2000; 20(9): 2094-2099 and Arterioscler Thromb Vasc Biol. 18:1386-1392, 1998) and which provide additional teachings of the role of CRP in the arterial intima and show that CRP frequently colocalizes with the terminal complement complex in the intima of early atherosclerotic lesions of human coronary arteries. As such, targeting CRP will likely be useful in imaging atherosclerotic lesions at an early stage of atherosclerosis. Drugs designed to treat atherosclerosis may be added to the gadolinium-based complexes to achieve an effective intervention of the disorder at an early stage.

C. rHDL Moieties as Drug Delivery Vehicles

As discussed above, in certain embodiments, it may be desirable to have rHDL moieties in which the metallic contrast agent is conjugated to a component of the core of the HDL, such as e.g., a cholesteryl ester. Methods and compositions for making DTPA mono- and di-stearyl esters corresponding to metal, e.g., gadolinium chelates, or non-metals, e.g., iodine, are known to those of skill in the art and have previously been described (G. W. Kabalka et al., *Magnetic Resonance in Medicine* 8 (1988), 89-95; Torchilin V P. Liposomes as carriers of contrast agents for in vivo diagnostics. In: Lasic D D, D. P, eds. Medical applications of liposomes. Amsterdam: Elsevier, 1998:515-543.) Such methods may be used to produce rHDLs in which the rHDL comprises a targeting moiety at the surface and a metallic or non-metallic agent in the core. Such compositions may be useful, for example, to target the imaging agent to a specific site and to later apply an enzyme or other composition that would promote the metabolism or breakdown of the HDL particle, such as a lipoprotein lipase, cholesteryl ester transfer protein or a phospholipid transfer protein, to effect release the imaging agent in a control manner. Imaging agent can be released enzymatically. The characterization of the signal can change and be used to improve detection of any disease/disorder or any organ in the body. Such a composition would be useful is the imaging agent was being used to track the delivery of a drug or other therapeutic component to a specific in vivo site.

Therefore, it is contemplated that the compositions of the present invention, in addition to comprising a targeting moiety and a metallic or non-metallic contrast agent, also may comprise a third agent that is being delivered to effect a therapeutic outcome. Any agent can be delivered in this manner and methods of using lipoproteins to deliver drugs are well known to those of skill in the art (Rensen et al. Adv. Drug. Del. Rev. 47: 251-276, 2001.) The therapeutic agent that may be used in the compositions of the invention is limited only by the features that it should not destroy the structural integrity of the rHDL particle or render it larger than 18 nm. Further, the drug should be such that it does not quench or otherwise interfere with the signal generated by the metallic or non-metallic ion.

D. Methods of Using the rHDL

The rHDL compositions of the present invention will be useful in any MRI methods. These compositions will provide effective delivery of a contrast agent for MRI to an in vivo site. In particularly preferred embodiments, the compositions are used to image atherosclerotic plaques. Such techniques have previously been used in pigs, primates and humans as well as mice and other animals to document, e.g., progression and regression of atherosclerosis in vivo (Skinner et al., Nature Medicine. 1995; 1:69-73; McConnell et al., Arterioscler Thromb Vasc Biol. 1999; 19:1956-9; Worthley et al., Circulation. 2000; 101:586-9; Worthley et al., Circulation. 2000; 102:II-809; Johnstone et al., Arterioscler Thromb Vasc Biol. 2001; 21:1556-60; Helft et al., J Am Coll Cardiol. 2001; 37:1149-1154; Helft et al., Circulation. 2002; 105:993-8; Lin et al., J of Magn Reson Imaging. 1997; 7:183-90; Worthley et al., Circulation. 2000; 101:2956-2961; Corti et al., J Am Coll Cardiol. 2002; 39:1366-1373; Kaneko et al., Circulation. 1996; 94:I-346. Abstract; Toussaint et al., Circulation. 1996; 94:932-8; Yuan et al., Circulation. 1998; 98:2666-71; Coulden et al., Heart. 2000; 83:188-91; Hatsukami et al., Circulation. 2000; 102:959-64; Fayad et al., Circulation. 2000; 101: 2503-2509; Fayad et al., Circulation. 2000; 102:506-510; Botnar et al., Circulation. 2000; 102:2582-7; Corti et al., Circulation. 2001; 104:249-52; Yuan et al., Radiology. 2001; 221:285-99; Yuan et al., Clin N Am. 2002; 12:391-401; Jaffer et al., Arterioscler Thromb Vasc Biol. 2002; 22:849-54; Ouhlous et al., J Magn Reson Imaging. 2002; 15:344-51; Fayad et al., Neuroimaging Clin N Am. 2002; 12:461-71; Kim et al., Circulation. 2002; 106:296-9; Corti et al., Circulation. 2002; 106:2884-7; Cai et al., Circulation. 2002; 106: 1368-73; Johnson et al., Magnetic Resonance Quarterly. 1993; 9:1-30; Weissleder, Nature Rev Cancer. 2002; 2:11-8). Any such techniques may now be modified and conducted using the compositions of the present invention.

In addition, it is contemplated that, as HDLs are found circulating within the blood, the compositions of the invention may be used in imaging other tissues and sites within the body. As HDLs have the advantage of not being atherogenic, these compositions may be used in blood pool analyses to facilitate imaging of, e.g., myocardial and cerebral ischemia, pulmonary embolism, vascularization of tumors, tumor imaging, tumor perfusion, and the like. Given that the rHDL compositions of the invention comprise targeting agents, rHDLs may be designed to target any site within the body that contains a site-specific marker. As HDL is able to enter into interstitial fluid in general (i.e., across the endothelial layer of all blood vessels), the rHDL of the invention may be used to deliver imaging agents and drugs to any site.

The compositions will generally be injected into the animal to be imaged. By way of example, and in order to test the efficacy of the rHDL compositions, the rHDL compositions may be injected into mice or other test animals and their targeting to a site of interest may thus be determined. Preferably, prior to injection into mice, the rHDL will be tested for pyrogens. The initial volume to be injected is not expected to exceed ~0.3 ml per mouse, based on the projected rHDL dose of ~8 mg apoAI per mouse and previous literature indicating that rHDL mixtures containing ~26 mg apoAI/ml can be prepared and injected without difficulty (Shah et al., Circulation. 2001; 103:3047-50). The inventors have injected this volume routinely by jugular vein. This route has the added advantage of allowing an increase in the volume of injectate, in case it becomes necessary to increase the amount of Gd to increase the signal being generated.

Those of skill in the art also routinely monitor in vitro relaxivity measurement for contrast agents. It is contemplated that the contrast agents in the imaging compositions of the present invention have a greater relaxivity than the metallic contrast agents being administered through conventional methods because of the substantial load of Gd on rHDL. Any increase in relativity of the instant contrast agents as compared related compositions prepared in other non-HDL vehicles will be an advantageous property of the compositions of the present invention. Preferably, there is a 30-250% greater relaxivity of the present compositions as compared to those known to those of skill in the art. Thus, the higher relaxivities coupled to the specific targeting of the contrast agent using the rHDL compositions of the invention provide an important advance (advantage) in comparison to the known NMR contrast agent compositions.

In specific embodiments, in vitro relaxivity measurements of rHDL-DTPA-PE-Gd will be prepared in saline with different concentrations from 0-3 mM in 1.0 ml centrifuge tubes. The samples will be placed in a 30 mm diameter birdcage coil and placed in the 9.4T MR system. All experiments will be performed at 37° C. T1 relaxation data will be collected with a spin-echo sequence with a variable TR (300, 800, 1500, 2000, 3000 msec) and with a TE of 12.8 msec. T1 values of the samples will then be calculated from a 3 parameter exponential fit and plotted as 1/T1 vs. Gd concentration. The slope of this line will be molar relaxivity, R1. This would be used to perform quality control and dosage adjustments.

Interstitial penetration of the particles of the invention reflects the traversal across endothelium (required for entry into plaques). In order to assess this parameter, groups of young adult apoE-KO (n=15) and WT (n=15) mice are administered one of the following: $^{125}$I-labeled native human HDL (positive control), $^{125}$I-labeled rHDL, $^{125}$I-labeled Gd-rHDL, or $^{125}$I-human VLDL (too large to significantly cross the endothelium; negative control) (Sloop et al., J Lipid Res. 1987; 28:225-37; Vessby et al., J Lipid Res. 1987; 28:629-41). The lipoproteins may be labeled in either the apoAI (HDL) or apoB (VLDL) moieties using a standard iodination protocols (Fuki et al., J Clin Invest. 1997; 100:1611-22). To simulate the first series of imaging studies, each mouse will receive at least $10^{17}$ lipoprotein particles. The $t_{1/2}$ for HDL-apoAI in the circulation of a mouse is roughly 10 h (Tape et al., Biochim Biophys Acta. 1990; 1043:295-300). Thus, during the 10th hour after injection (i.e., from 9 to 10 h after injection), a suction blister will be induced on the back of each mouse, following a standard procedure used extensively in rodents (and humans) to induce the extravasation of interstitial fluid (e.g., see Vessby et al., J Lipid Res. 1987; 28:629-41; Herfst et al., Arch Dermatol Res. 1978; 263:325-4). At 10 h (i.e., ~1 half-life of native HDL) after injection, interstitial fluid will be harvested from each suction blister, and then the mice will be sacrificed and plasma samples taken for gamma counting. Based on the predicted physical properties of the native and rHDL particles, both are expected to exhibit ratios of interstitial-to-plasma concentrations of approximately 1:3. In contrast, the labeled VLDL should be almost entirely excluded from the interstitial space (Sloop et al., J Lipid Res. 1987; 28:225-37; Vessby et al., J Lipid Res. 1987; 28:629-41). If the Gd-rHDL particles exhibit substantially less interstitial penetration than $^{125}$I-HDL, the size and/or surface charge of the reconstituted particles may require adjustment.

In certain embodiments it may be desirable to monitor the iodistribution, autoradiography, and metallic contrast ion content of the rHDL compositions of the present invention. In exemplary methods a group of apoE-KO (n=15) and WT (n=15) mice will are fed on the well-known "Western diet" for 16 weeks (to accelerate the formation of lesions in the aorta of apoE-KO mice). The imaging compositions of the present invention, e.g., rHDL-DTPA-PE are labeled with $^{111}$In (rHDL-DTPA-PE-$^{111}$In) using standard methods (Phillips et al., Adv Drug Deliv Rev. 1999; 37:13-32) and injected via the tail vein. After 4 h, 12 hrs, and 24 hrs post injection, randomly selected mice (5 in each group) are sacrificed and the following tissues harvested: blood, heart, lungs, liver, kidneys, spleen, stomach, bone, muscle, skin, urine and aorta.

The organs are weighed and the radioactivity counted. The organ biodistribution values is expressed as % injected dose/g tissue (% ID/g). The aorta should be subjected to further study. As lesions will be diffusely distributed, half of the aorta is reserved for sectioning of lesioned and non-lesioned areas and the other half opened longitudinally and stained with Sudan IV to visualize lesions. Autoradiographic images are obtained using routine techniques of exposure of the stained aorta to Kodak Biomax high-speed film for a desired period of time, e.g., 1 week. By comparing the location of the autoradiographic signals to the Sudan staining, it is possible to determine the presence of rHDL and if there is enrichment in lesioned vs. nonlesioned areas. In the absence of a targeting molecule (or other strategies to promote retention of the rHDL in lesions) detectable, but relatively low, signals are expected, including at lesion sites. An advantage of the compositions of the present invention as compared to the use of iron particles or small micelles, which also can enter lesions, but are retained "non-specifically," the molecules of the present invention may be specifically targeted to a specific site. Thus, while iron particles and small micelles produce only non-specific signaling, the molecules of the present invention provide an excellent alternative for signal enhancement based on the presence of specific molecules of interest within the plaque.

The portions of aorta reserved for sectioning may be processed using methods known to those of skill in the art, (e.g., Rong et al., Circulation. 2001; 104:2447-52; Fayad et al., Circulation. 1998; 98:1541-7; Choudhury et al., Atherosclerosis. 2002; 162:315-21; Choudhury et al., J Magn Reson Imaging. 2003; 17:184-189), but with the addition here of autoradiography and immunostaining for human apoAI. Human-specific monoclonal antibody against apoAI for this purpose is known to those of skill in the art. These data allow confirmation of the entry of the rHDL into the aortic wall and to determine its distribution within the tissue. These assays (on Sudan-stained intact aorta as well as on aortic sections) may be repeated for the rHDL engineered to promote its retention in plaques.

In a parallel mouse study as above (15 apoE-KO and 15 WT), the Gd content in the aorta after sacrifice is assessed by inductively coupled plasma (ICP) analyses (Gailbraith Labs, Inc. (Knoxville, Tenn.) (Glogard et al., Int J Pharm. 2002; 233:13140; Fossheim et al., Magn Reson Imaging. 1999; 17:83-9; Tamat et al., Pigment Cell Res. 1989; 2:281-5).

Figure 3:
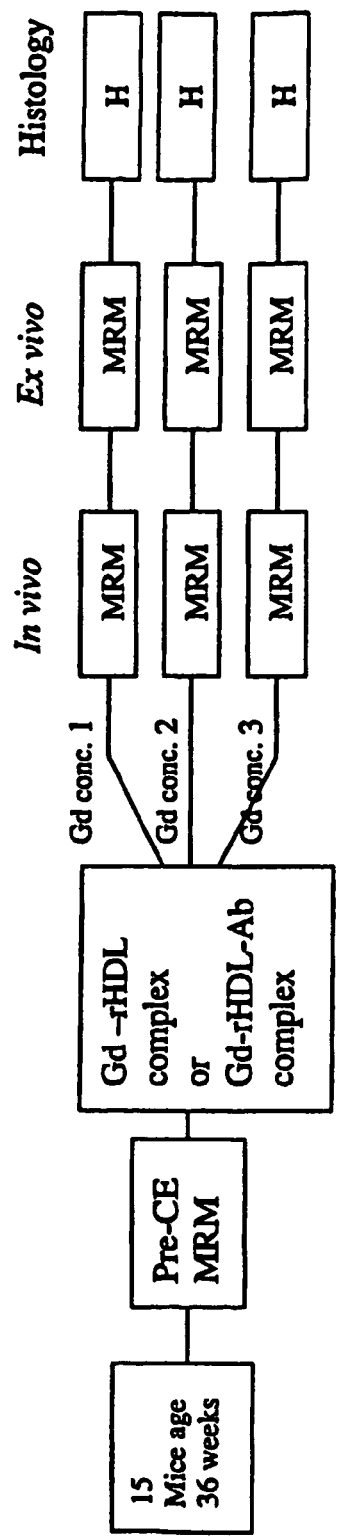
FIG. 3. Experimental outline for the evaluation of the Gd-rHDL and Gd-rHDL-Ab complex contrast agent in apoE-KO mice with advanced atherosclerotic lesions. The outline applies to both apoE-KO and wild-type (WT) mice. A total of 30 mice (15 apoE-KO and 15 WT) 36 weeks old (32 weeks on WD) are used to test the Gd-rHDL complex; and another 30 mice are used for GdrHDL-Ab complex. Three different Gd complex concentrations (conc.) will be used. Ab=antibody.

Methods of performing in vivo MRM also may be used to test the efficacy of the present imaging compositions. Animals (15 apoE-KO; and 15 WT) may be treated as discussed above. (FIG. 3). Contrast agent injection of rHDL-DTPA-PE-Gd and in vivo MRM may be performed. Briefly, to assess the plaque the following MRM may be conducted (FIG. 3): 1) in vivo multicontrast black-blood pre-contrast enhanced (CE) MRM; 2) in vivo postcontrast (rHDL-DTPA-PE-Gd complex) CE MRM black-blood T1W imaging; and 3) ex vivo post-CE MRM. Multiple different contrast agent concentrations should be tested based on the relaxivity and biodistribution results. As noted herein, initial injections should preferably contain ~$10^{18}$ Gd ions, delivered as rHDL-Gd-DTPA-PE in an injection volume of ~0.3 ml per mouse.

Following in vivo experiments, ex vivo MRM also may be performed. The animals are euthanized, and perfused fixed at physiological pressure. The heart is harvested and fixed in 4% paraformaldehyde for at least 24 hr. Ex vivo MRM experiments are performed using a 10-mm birdcage coil using methods previously described (Itskovich et al., Magn Reson Med. 2003; 49:381-5; Fatterpekar et al., AJNR Am J Neuroradiol. 2002; 23:1313-1321). Briefly, each specimen will be washed and placed in an 8-mm polyethylene tube filled with Fomblin (perfluoropolyether, Ausimont USA Inc., Morristown, N.J.) and sealed to prevent air bubbles. The use of Fomblin limits tissue dehydration and MR artifacts on the surface of the specimen. Multicontrast MR images are acquired with same parameters as in the in vivo sequence but now with a 25-50 µm/pixel resolution. The specimens may further be histologically analyzed.

The apparati for use in imaging tissues are not considered limiting to the invention and the compositions may be used in any MRI technique known to those of skill is the art. Simply by way of example, those of skill in the art referred to e.g., U.S. Pat. Nos. 6,590,391; 6,591,128; 6,586,933; 6,580,936; 6,600,401; 6,611,143; 6,541,973, which describe MRI apparati in detail. These are merely exemplary descriptions and those of skill in the art will be aware that other imaging techniques may be used in other to perform the methods of the present invention using the compositions described herein.

The methods described in U.S. Pat. No. 6,498,946 may be particularly useful in MRM and atherosclerotic plaque imaging as discussed infra. In particular embodiments, the compositions of the present invention may be used to assess the efficacy or dosing of a particular existing drug. For example, in the case of atherosclerosis, the atherosclerotic lesion size or composition may be monitored prior to and after the administration of a given drug treatment to assess whether the treatment is effective at reducing the size or composition of a lesion.

E. Pharmaceutical Compositions and Kits comprising rHDL

It is contemplated that that rHDL compositions of the invention will be used in MRI or other imaging method in any in which it is desired to obtain an image of an internal site. Thus, the compositions of the invention will be administered, in vivo. Therefore, it will be desirable to prepare the compositions of the invention as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the rHDL to deliver an appropriate amount of metallic or non-metallic contrast agent, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As HDL is normally found circulating in the system of an animal, it is contemplated that the rHDL imaging compositions of the invention should not produce such an adverse effect. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the rHDL of the invention (e.g., so long as the agent does not destroy the structural integrity of the molecule or quench the signal of the metallic ion), its use in the compositions of the invention is contemplated. Supplementary contrast enhancing ingredients also can be incorporated into the compositions.

The term "effective amount" as used herein refers to any amount of the rHDL compositions of the invention that produce a reproducible and evaluable image of a given in vivo site. Thus, it should be understood that the effective amount of the rHDL may vary depending on the size of the animal, the site at which the composition is to be administered and the route of such administration. The field of MRI technology is advanced and technicians are experienced in determining whether a given composition is producing the desired intensity of signal. In specific embodiments discussed in the examples, it was determined that 10 Gd-DPTA-PE molecules/rHDL particle may be an exemplary dose to image atherosclerotic plaques in mice. It should, however, be understood that more or less than 10 Gd-DPTA-phospholipid molecules/rHDL particle also are contemplated. For example, the imaging compositions may advantageously comprise 1, 2, 3, 4, 5, 6, 7, 8, 9, 10, 11, 12, 13, 14, 15, 16, 17, 18, 19, 20 or more Gd-DPTA-phospholipid particles/rHDL molecule. It should be understood that the number of Gd-DPTA-phospholipid/rHDL particle is limited only by how many such molecules can be incorporated into the rHDL particle without destroying the structural integrity of the HDL or making it larger than would be effective as an imaging compositions of the invention (i.e., larger than 18 nm.)

With respect to the administration of rHDL, and using the apoAI content of the rHDL as a measuring parameter, it is contemplated that the amounts of rHDL administered to mice may comprise 8 mg, 10 mg, 12 mg, 14 mg, 16 mg, 18 mg, 20 mg, 22 mg, 24 mg, 26 mg, 28 mg, or even 30 mg of apoAI. Such compositions can be extrapolated to humans. For Example, infusion of rHDL compositions of the present invention that comprise 45 mg ApoAI protein/kg body weight of animal to be treated will be particularly useful. The compositions may thus comprise 40 mg ApoAI protein/kg, 45 mg ApoAI protein/kg, 50 mg ApoAI protein/kg, 55 mg ApoAI protein/kg, 60 mg ApoAI protein/kg or more. Given the characteristics of HDLs discussed herein above and in reference to Table 1, those of skill in the art should readily be able to determine the amounts of other HDL components being administered in a given dose.

In certain embodiments, the amounts of phospholipid doses that can be used in the compositions described herein may be inferred from experience in administering Intralipid™ (Kabivitrum Inc., California and Stockholm, an aqueous suspension of lipid droplets that is sterile and suitable for intravenous feeding of patients. Other similar lipid solutions that may provide guidance as to amounts and proportions of lipids that may safely be provided to patients include Nutralipid™(Pharmicia, Quebec), Liposyn™ (Abbot Labs, Montreal)). These compositions are used by the biomedical optics community as a scattering media in optical experiments. In other embodiments, the amount of rHDL that is administered in the imaging embodiments of the present invention is guided by the typical concentrations of HDL in human plasma, and the dose used in the imaging modalities described herein may use up to double the concentration of HDL normally found in human plasma. Those of skill in the art are aware of amounts of HDL that may typically be administered. See e.g., Nissen et al., JAMA. 290(17):2292-300, 2003, which is incorporated herein by reference as showing parameters for the selection of patients that receive HDL and amounts of HDL that may typically be administered. For example, the patients may receive between 15 mg/kg or 45 mg/kg of rHDL. Those of skill in the art will be able to vary the amount administered depending on the size and weight of the patient and the like.

The rHDL particles of the present invention are intended for use in any MRI regimen that is conventional in the art, including MRI of humans. Administration of the imaging compositions according to the present invention will be via any common route used in imaging so long as the target tissue is available via that route. This includes administration by orthotopic, intradermal subcutaneous, intramuscular, intraperitoneal, intrathecal, or intravenous injection. Alternatively, oral, nasal, buccal, rectal, vaginal or topical administration also are contemplated. For imaging atherosclerotic plaques intravenous injection is contemplated. Such injections compositions would normally be administered as pharmaceutically acceptable compositions that include physiologically acceptable carriers, buffers or other excipients. For imaging of tumors, direct intratumoral injection, injection of a resected tumor bed, regional (i.e., lymphatic) or general administration is contemplated. It also may be desired to perform continuous perfusion over hours or days via a catheter to a disease site, e.g., a tumor or tumor site.

The imaging compositions of the present invention are advantageously administered in the form of injectable compositions either as liquid solutions or suspensions; solid forms suitable for solution in, or suspension in, liquid prior to injection may also be prepared.

The rHDL compositions of the invention can be sterilized by heat, radiation and/or filtration, and used as such, or the compositions can be further dehydrated for storage, for instance by lyophilization. The dehydrated material in form of a powder from which the MRI contrast agent may be produced by admixing the powder with a portion of carrier liquid and shaking. For practical application the compositions of the invention in the medical field, it is contemplated that the dried components and the carrier liquid can be marketed separately in a kit form whereby the contrast agent is reconstituted by mixing together the kit components prior to injection into the circulation of patients.

A typical composition for such purpose comprises a pharmaceutically acceptable carrier. For instance; pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, buffered solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the imaging composition may be adjusted according to well known parameters the amount and degree of signal intensity observed and required.

The individual components of the rHDL imaging compositions of the present invention may be provided in a kit, which kit may further include instructions for formulating and/or using the imaging agents of the invention. Such a kit will comprise a first composition comprising a metallic or non-metallic contrast agent, a second composition comprising a phospholipid covalently linked to a chelating moiety, a third composition comprising HDL apolipoproteins, a fourth composition comprising a free phospholipid, and a fifth composition comprising a sterol. The kit may further comprise a sixth composition comprising HDL core lipids (e.g., cholesteryl ester, and TAG).

The kit also may comprise a device for delivering the composition to a mammal.

EXAMPLES SECTION

Example 1

Methods and Stoichiometry of Reconstitution of rHDL

As discussed herein throughout, the present invention is related to imaging compositions that comprise rHDL as a backbone structure. The apolipoproteins for the production of the rHDL composition may be derived from an animal as a source of the apolipoproteins for the production of the rHDLs. In a preferred method for the producing rHDLs the apolipoproteins are from human HDL. Human HDL may be isolated from pooled human plasma by sequential density gradient ultracentrifugation to capture material between the densities of 1.063 and 1.21 g/ml, following standard protocols for separating HDL known to those of skill in the art Havel et al., *J Clin. Invest.*, 34:1345-1353, 1955; Shamir et al., *J Clin Invest.* 97(7):1696-704, 1996. The purity of the isolated HDL may be confirmed using techniques such as SDS-PAGE. Such techniques should show an absence of apoB, the major protein of VLDL and LDL, and an absence of albumin. In the event that there is contamination of a purified HDL preparation by these proteins, such contaminants may be removed by re-floatation of the HDL. Of course, those of skill in the art also may be able to obtain purified HDL from commercial sources such as Sigma Chemical Co. (St. Louis Mo., Catalog No. 18039 (HDL in saline/EDTA) Catalog No. 80917 for lyophilized HDL).

The purified HDL apolipoproteins can then be reconstituted with two different sets of lipids. As the major circulating form of HDL is spherical, and spherical rHDL has been successful in delivering drugs to tissues, it is preferable to reconstitute HDL as spherical particles. Thus, the first of lipids in which the apolipoproteins may be reconstituted in are lipids that will produce spherical HDL particles. This set includes surface lipids, chiefly phospholipids, plus core lipids, chiefly TAG and cholesteryl ester. This composition preferably should mimic natural HDL and generate small spherical particles (~10 nm diameter). Particular reference is made to Table 1 above, and Rensen et al. 2001, for characteristics of circulating HDL that should be mimicked.

Alternatively, it may be desirable to produce a discoidal rHDL particle. This is achieved with the second set of lipids for reconstitution, which is limited exclusively to surface lipids (i.e., preparing rHDL composition that lacks the core lipids). At high protein:lipid ratios, this composition generates small discoidal particles, which are essentially segments of lipid bilayers with the edges stabilized by the HDL apolipoproteins. These disks are about 10 nm in diameter and 5.5 nm thick and are thought to resemble nascent HDL as it is secreted from the liver. As discussed further below, discoidal reconstituted particles are an attractive alternative to spherical rHDLs in those circumstances in which the loading to the HDL particles with the imaging or targeting agent makes the spherical HDL particles too large (Shamir et al., J Clin Invest. 1996; 97:1696-704). Discoidal particles are made by a standard sonication method (Lund-Katz et al., Biochemistry. 1986; 25:1562-8) that has also been used for the incorporation of drugs (de Vrueh et al., Antimicrob Agents Chemother. 2000; 44:477-83).

The composition of the spherical synthetic rHDL compositions of the present invention resembles that of native human plasma-derived HDL. In order to achieve the exemplary reconstitution described herein, purified native HDL was delipidated with ethanol/diethyl ether (3:2, vol/vol) at 0° C., and the total HDL apolipoproteins were reserved for the reconstitution step. While it is contemplated that native HDL lipids from the ethanol/ether extraction also may be used in the reconstitution, it is preferable to use defined lipids from commercial sources, in order to allow maximal control and reproducibility for the incorporation of the Gd-DPTA-PE chelates. As shown by many investigators, the use of defined lipids does not introduce significant differences in HDL structure or function, as compared to the use of native HDL lipids. High-quality, defined lipids are available from commercial sources such as e.g., from Avanti Polar Lipids (Alabaster, Ala.).

In addition, for greater control and reproducibility between batches, purified apoA-I instead of total HDL apolipoproteins also may be used. ApoAI is purified from the other HDL apolipoproteins by gel filtration through a Sephacryl S-200 column after delipidation by ethanol/ether. ApoA-I or other apolipoproteins to be used in the rHDLs of the invention also may be obtained from commercial sources (e.g., Sigma Chemical Co., St. Louis, Mo.; or PerImmune Inc., Rockville, Md.).

Based on the weight % composition of the components of native HDL (Table 1 above) and the molecular weights of POPC (palmitoyl oleoyl PC), triolein (the triglyceride component), cholesterol, cholesteryl oleate (cholesteryl ester) and apoAI, the molar composition of the rHDL, should be (PC:CE:C:TG:apoAI):100:62:25:11:2 to simulate the native particles (assuming apoAI represents approximately 50% of HDL protein). For ease of manufacture and storage, these components, particularly POPC, were selected to be relatively resistant to lipid peroxidation, yet they remain fluid within the reconstituted particle at body temperature.

To produce reconstituted particles, the lipids (separately maintained in stock solutions of chloroform or hexane) are combined in the appropriate molar amounts in a glass tube and dried under nitrogen and then high vacuum to remove all traces of organic solvents. After suspension in Tris pH 8.0 buffer, the lipids are dispersed by sonication, followed by low speed centrifugation to remove any shards from the sonicator probe tip. ApoAI (in Tris pH 8.0 buffer) is then added (to 2 mol %) and incubated at 37° C. for 30 min, after which the mixture is again sonicated and re-centrifuged at low speed. The resulting dispersion is filtered (0.22 µm), and the rHDL isolated by size exclusion chromatography through a Superose 6 column. Typically, this procedure results in spherical HDL particles of 7-9 nm diameter with approximately 80-90 phospholipid molecules and 2 apoAI molecules per particle (Braschi et al:, J Lipid Res. 1999; 40:522-32; Ramsamy et al., J Biol Chem. 2000; 275:33480-6). Extrusion, cholate dialysis, and/or shear methods e.g., using microfluidizers also can be used for reconstitution.

As PE is readily incorporated into liposomes (at least 50% by weight of the phospholipid content (Grant et al., Magn Reson Med. 1989; 11:236-43) and HDL (at least 10 mole %, (Lund-Katz et al., Biochemistry. 1986; 25:1562-8)) and owing to its close structural similarity to PC, Gd-DPTA-PE should readily be incorporated into the rHDL particles using co-sonication (Lund-Katz et al., *Biochemistry.* 1986; 25:1562-8).

In preparing the rHDL compositions, it may be necessary to consider is how much chelate should be incorporated into each HDL particle. Administration of $10^{18}$ Gd ions per mouse is sufficient to obtain high-quality images of lesional aorta (Nunn et al., Q J Nucl Med. 1997; 41:155-62; Aime et al., J Magn Reson Imaging. 2002; 16:394-406; Lauffer et al., Magn Reson Q. 1990; 6:65-84; Ahrens et al., Proc Natl Acad Sci USA. 1998; 95:8443-8). Using rHDL compositions of the present invention, this dose of Gd is easily accomplished by incorporating 10 Gd-DPTA-PE molecules per rHDL particle and administering approx. $10^{17}$ particles per mouse. To maintain particle structure, the Gd-DPTA-PE would replace POPC, molecule for molecule. Based on the stoichiometry given in the preceding paragraph, $10^{17}$ rHDL particles contain approximately 8 mg of apoAI and 13 mg of phospholipid. Because rHDL and phospholipid liposomes have been used to deliver far higher doses to mice (up to 13 mg of apoAI (Shah et al., Circulation. 2001; 103:3047-50) and 30 mg PC per mouse (Williams et al., Arterioscler Thromb Vasc Biol. 2000; 20:1033-9), the dose of rHDL proposed for use here (i.e., 10 Gd-DPTA-PE molecules/rHDL particle) should be readily achievable without toxicity.

Producing Discoidal rHDL.

A standard discoidal reconstituted HDL particle (approximately 10 nm in diameter) contains approximately 100/1 lipid to protein mol ratio. These particles are relatively homogeneous in size and normally do not require fractionation by gel filtration. In order to prepare these particles one employs a stock concentrations as: POPC (Avanti): 20 mg/ml in chloroform; human apo A-I: 1 mg/ml in TRIS buffered saline (TBS).

Based on the above values, the starting composition (mg/glass tube) for a preparation containing 1 mg apo A-I: POPC: 2.7 mg/tube, this equals 0.134 ml of stock POPC; apo A-I: 1 mg/tube, this equals 1.0 ml of apo A-I stock solution. The lipid is dried as a film on-the tube wall, under nitrogen. The tube is then placed in a vacuum oven for approximately 2 h to remove any remaining organic solvent. Meanwhile, the protein is solubilized in 6 M Gdn HCl and then dialyzed overnight into TBS, pH 7.4. Preferably, the protein concentration is determined at this point (A280=1.13 for a 1 mg/ml solution or use Lowry assay). All the following values are based on a protein concentration of 1 mg/ml.

The tube is removed from the vacuum oven and 0.176 ml of TBS (pH 7.4) is added to the lipids, and vortex for approx. 1 minute or until all lipids have come off the glass wall and formed a turbid suspension. 0.094 ml sodium cholate (stock solution of 30 mg/ml in TBS) is added, and the mixture is vortexed for another 1-2 minutes. The mixture is then incubated at 37° C. for 1.5 h, vortexing for a few minutes every 15 minutes. If the solution has not turned clear after approximately 30 minutes incubation, the mixture is sonicated in a water-bath sonicator for 5-10 minutes, the solution should go clear indicating that PC/cholate micelles have formed. The mixture is then allowed to incubate for the remainder of the 1.5 h with vortexing every 15 minutes. After the 1.5 h incubation, the protein solution is added to the lipids (final volume=1.0+0.176+0.094=1.27 ml). This mixture is further vortexed gently to avoid excessive foaming, for about half a minute and then incubated at 37° C. for one hour.

After the incubation, the dialysis to removed the sodium cholate is initiated at 4° C. using a 14,000 molecular weight cut-off membrane. Typically, this requires 2-3 days depending on the amount of cholate used. The micelles are dialyzed against 4 liters of TBS X 6 changes to remove all the cholate.

In order to scale-up the preparation for production of larger quantities, the inventors determined that greater particle homogeneity is achieved if the final apo A-I concentration before the dialysis step is maintained at approximately 1 mg/ml. The ultimate samples of particles can be concentrated using Millipore centrifugal filters.

Labelling of HDLs with Non-Metallic Atoms

The following is an exemplary description of labeling of HDLs using iodine or fluorine. Iodine in all isotopes ($^{123}I$, $^{125}I$, $^{127}I$, $^{131}I$) can be successfully linked to Apo A-I protein using IODO-BEAD Iodination reagent (Pierce, Rockford, Ill.) in good yield. Once linked, the labeled protein can be reconstituted with lipids to form the Iodinated HDL. Iodinated HDL can be used for PET/SPECT and CT indications. Below is a brief description for protein labeling:

1. Wash beads with 500 µl of reaction buffer per bead. Dry the bead(s) on filter paper.
2. Add bead(s) to a solution of carrier-free $^{123}I$, $^{125}I$, $^{127}I$, $^{131}I$ (approximately 1 mCi per 100 µg of protein) diluted with reaction buffer and allow to react for 5 minutes.
3. Dissolve or dilute protein in reaction buffer (TBS) and add to the reaction vessel. Allow the reaction to proceed for 15 minutes.
4. Stop the reaction by removing the solution from the reaction vessel.
5. Dialyze the solution.

For labeling of lipids, the protocol used is similar to the protocol used for labeling lipids with metallic agents.

To incorporate $^{18}F$ isotope in HDL we will introduce $^{18}F$-fluorodeoxyglucose (FDG a common PET agent) into the core of HDL. Since FDG is neutrally charged it should easily being incorporated into the core. The material could be produce as follows:

1. Add ApoA-I to the reaction buffer (TBS) that contains a mixture of lipids and FDG.
2. Sonicate.
3. Dialyze the solution.

Example 2

Derivatization of Phospholipids for Use in rHDL Compositions of the Invention.

The rHDL compositions of the present invention will be designed to comprise phospholipids that have been derivatized with either the metallic ion chelate, the non-metallic imaging agent or, with a targeting components. While the following discussing is based on PE derivatives, it should be understood that any phospholipid, and particularly, PC, PA, PS, PI, PG, CL and SM could also be derivatized in similar fashion.

In certain exemplary embodiments of the present invention, PE derivatives for incorporation into rHDL are Gd-DTPA-PE, biotinylated PE, and poly-L-lysine-PE. The purpose of these phospholipid derivatives is to allow specific agents to be incorporated onto the surface of the rHDL compositions of the invention. Each PE (or other phospholipid) derivative is anchored via its hydrophobic fatty acyl chains into the rHDL surface. Each PE derivative projects a finctional moiety from the rHDL surface, to which the metallic or non-metallic imaging contrast agent may be attached. In specific embodiments, that contrast agent is, for example, Gd (for MR contrast) is iodine or bromine (for CT), 111In, 99 mTc (for gamma-scintigraphy), fluorescein (for optical imaging). In other embodiments, it is contemplated that the rHDL entities of the invention also will comprise a targeting agent for molecular targeting of the rHDL imaging particles. The targeting agent, e.g., an antibody will be attached to a PE (or other phospholipid moiety) head group through a functional group. Preferably, the contrast agent and targeting agent are on separate phospholipid molecules within the rHDL.

Figure 2:
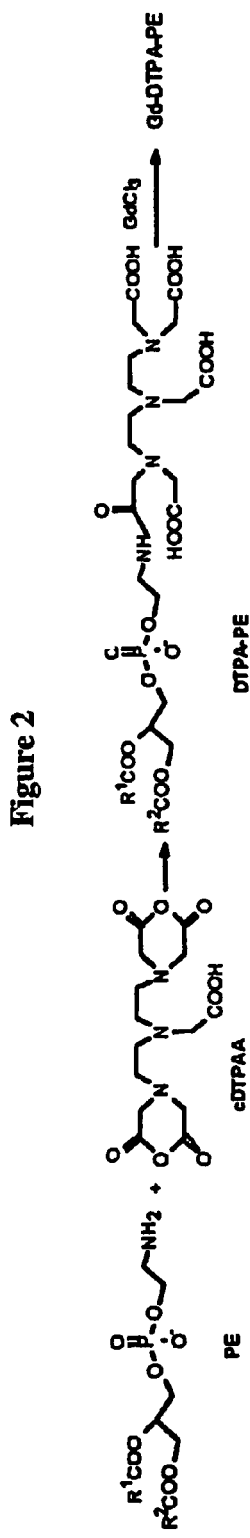
FIG. 2 Formation of Gd-DTPA-PE.

In specific examples, the metallic paramagnetic ion is Gd, which is attached to the PE covalently linked to DTPA, a chelating agent. Other metallic agents and chelating agents have been discussed above. The synthesis of DTPA-PE is routinely performed by incubating PE with cyclic DTPA anhydride (cDTPAA), followed by column chromatography purification. Gd incorporation is then achieved by treating gadolinium chloride hexahydrate (Aldrich, Milwaukee, WI) with DTPA-PE and purified Gd-DTPA-PE complexes using column chromatography. A schematic representation of this synthesis is depicted in FIG. 2.

To attach antibodies or other targeting agent, biotinylated-PE or other phospholipid (available from Avanti Polar Lipids) may be used. As with DTPA-PE, the biotinylated PE is substituted for PE during the reconstitution of HDL particles. In exemplary embodiments, the targeting agent is an antibody. The biotin group is exposed at the surface of the rHDL, so that antibodies conjugated to avidin and mixed with the rHDL will self-associate and be available for binding to their target antigens (e.g., see Lanza et al., Circulation. 2002; 106:2842-7).

In a particular embodiment, it may be desirable to increase the amount of contrast agent or targeting agent in the rHDL particle, but without producing a concomitant increase the mass of derivatized PE per particle. This may be necessary in the event that the mole % DPTA-PE that replaces the PE in the HDL disrupts the structure of the rHDL. As noted above, this is highly unlikely because DPTA-PE substitutes well for PE into related structures such as liposomes. Nevertheless, a feasible way to substantially lower the content of DPTA-PE in the rHDL is to use an established procedure in which a poly-L-lysine linker is attached to PE, so that at each epsilon-amino group, a DPTA moiety is covalently attached. In this way, less PE, but more Gd (and/or other metal), can be incorporated into the rHDL. Thus, it is contemplated that the use of the poly-L-lysine-PE will allowing multiple metallic ions to be chelated. This is a standard method that has previously been used in liposomal applications (e.g., see Torchilin et al., Adv Drug Deliv Rev. 2002; 54:235-52; Torchilin, Medical applications of liposomes. Amsterdam: Elsevier; 1998:515-543). Use of this strategy will facilitate a further increase in the amounts of signal intensity. Similarly, the same poly-L-lysine-PE can be used to load additional antibody molecules/rHDL (Slinkin et al., Bioconjug Chem. 1991; 2:342-8). Thus, it is contemplated that a single PE molecule will have multiple metallic contrast agents linked thereto, and/or multiple targeting agents linked thereto.

EXAMPLE 3

Production of Lipoprotein Apolipoprotein-I (LpAI)-Gadolinium Complexes

Gadolinium 1,2-Dimyristoyl-SN-Glycero-3-Phosphoethanolamine DiethyleneTriamine Pentaacetic Acid (Gd-DMPE-DTPA). 1,2-Dimyristoyl-SN-Glycero-3-Phosphoethanolamine diethylenetriamine pentaacetic acid (25 mg, 22.8 µmol) was heated to reflux with gadolinium triflate (7 mg, 22.8 µmol) in dry acetonitrile (4 mL) for 18 h. The solution was allowed to cool and the solvent evaporated to afford a pale yellow solid that was used without previous purification.

Preparation of Spherical LpA-I-Gd Complexes

Reconstituted LpA-I.Gd complexes were prepared by cosonication of POPC (palmitoyl oleoyl phosphatidylcholine), TAG (triglyceride, for example, triolein), FC (free cholesterol), C (cholesterol ester), ApoA-I and GdDMPEDTPA. Specific amounts of POPC, TG, C, FC and GdDMPEDTPA or other lipophilic gadolinium complexes in chloroform were dried under nitrogen into a 12×75 mm glass test tube and 800 µL of PBS was added. The lipid-buffer mixture was sonicated for 1 min in a 15° C. water bath, incubated for 30 min at 37° C., and sonicated again for 5 min. ApoA-I was subsequently added to the lipid suspension and the protein-lipid mixture was sonicated four times (1 min each time), punctuated by 1-min cooling periods. All LpA-I complexes were filterd through a 0.22 µm syringe tip filter and reisolated either by size-exclusion chromatography on a Superose 6 column or by sequential density gradient ultracentrifugation.

Example 4

Methods of Confirming the Configuration of the rHDL

Having produced the rHDL compositions as described herein above, it may be advantageous to determine the mole % of each component of the rHDL compositions of the invention. This may be determined by the biochemical assays known to those of skill in the art (Shamir et al., J Clin Invest. 1996; 97:1696-704). The Gd content is determined by inductively coupled plasma (ICP) analyses (Gailbraith Laboratories, Inc. (Knoxville, Tenn.) (Glogard et al., Int J Pharm. 2002; 233:131-40; Fossheim et al., Magn Reson Imaging. 1999; 17:83-9), and/or by size exclusion chromatography (gel filtration) through a calibrated column (e.g., Superose or Sepharose chromatography column).

The penetration of Gd-rHDL into the interstitial space, including the interior of atherosclerotic plaques, will be affected by particle size and to some extent by surface charge. Particle size will be determined by non-denaturing gel electrophoresis through 2-16% and 4-30% gels, as described by Williams & Scanu (Williams et al., Biochim Biophys Acta. 1986; 875:183-94). In addition, the size of the rHDL will be determined using Laser Light Particle Sizer (Model HPPS 500, Malvern Instruments Inc., Southborough, Mass.).

As discussed above, it is preferred that the Gd-rHDL should average 5-12 nm in diameter. Surface charge of these moieties may be assessed by agarose gel electrophoresis, as described in previous publications (Sparks et al., J Biol Chem. 1992; 267:25839-47; Sparks et al., J Lipid Res. 1992; 33:123-30). In all of the above methods, normal human HDL may be used as reference standard. Substantial deviations of either the size or surface charge from normal HDL could impair particle penetration into the interstitial space, which may be measured directly in vivo as described below.

In the event that the surface charge of the rHDL is substantially different from normal HDL and if this altered surface charge substantially decreases penetration of the particles into the interstitium in vivo, it is contemplated that small amounts of positively (basic) or negatively (acidic) charged lipids may be added as needed to restore a more natural total surface charge. With this modification, interstitial penetration will be achieved. In the event that the size of the rHDL (either with the Gd chelates or with the Gd-antibody-chelates) is substantially larger than normal HDL, accompanied by a large decrease in penetration into the interstitum in vivo, it is proposed that discoidal reconstituted particles (discussed above) should be used. This is because variants of the Gd chelates would expand the particles in a direction perpendicular to the surfaces, but not the edges, of the disks. Thus, the largest overall dimension would not increase. Of note, rHDL disks have also proven useful as drug delivery vehicles (Rensen et al., Adv Drug Deliv Rev. 2001; 47:251-76), so the technology is reasonably mature. Additionally, in order to reduce the size of the rHDLs comprising antibodies as the targeting moieties, it should be possible and desirable to use antigen-binding fragments of the antibody (e.g., Fab or other antibody fragments), rather than the whole antibody molecules, which would also reduce overall particle size.

Example 5

Use of rHDL in MRI in Mice

Model animals can be used to image atherosclerotic plaques, to test the efficacy of the compositions of the present invention. ApoE-KO and Wild Type (WT) mice in the C57B1/6 background weighing 15-40 g, (Jackson Laboratories, Bar Harbour, Me.) are preferably be used. After weaning (4 weeks of age) and a 2 weeks period on a regular chow diet, the apoE-KO mice will be fed a Western Diet (Research Diets, New Brunswick, N.J.) for up to 42 weeks.

Figure 4:
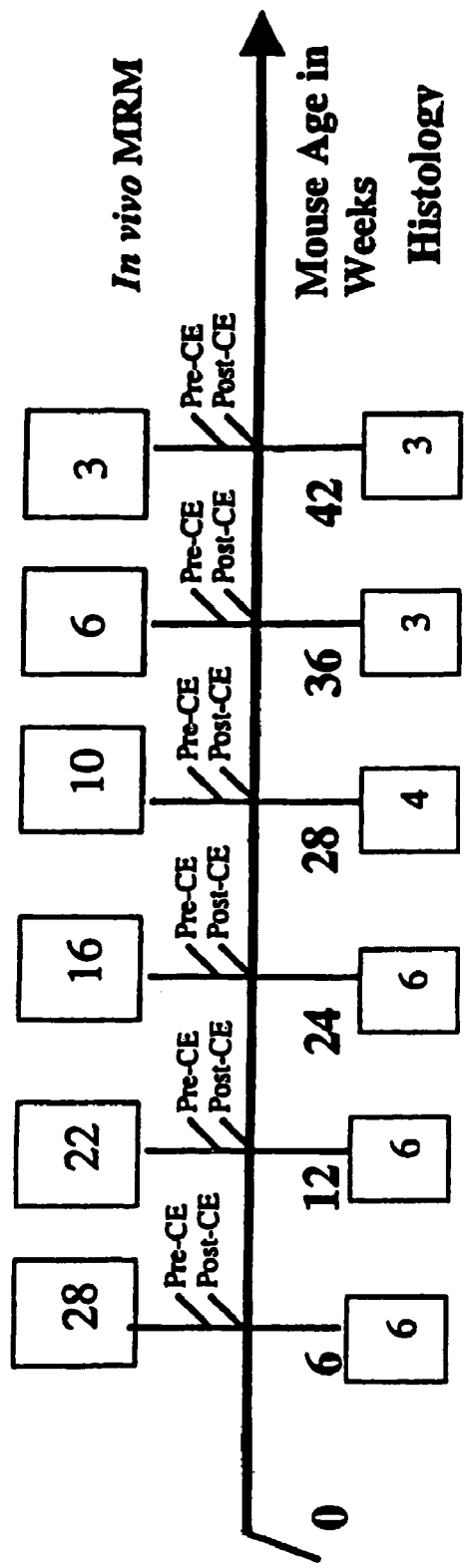
FIG. 4. Outline for evaluation of MRM analysis with and without Gd-DTPA. Figure details time line and number of mice in each group at different time points. In vivo pre and post-contrast enhanced (Gd-DTPA) MRM and histology analyses are performed. This time line applies to either the apoE-KO or wild-type (WT) mice. A total of 56 mice (28 apoE-KO and 28 WT) will be used.

The scheme for in vivo contrast enhanced (CE) MRM in the above mice is depicted in FIG. 4. Before MRM, an 27-ga. needle is inserted in the tail vein of the mouse and the needle is connected to a saline filled micro polyurethane catheter (Harvard Apparatus, Holliston, Mass.) with a Y-site connector, and attached to a syringe pump (Braintree Scientific Inc., Braintree, Mass.) while the other connector is attached to a saline-filled syringe for flushing before and after injection of the contrast agent. The animals are anesthetized with an isoflurane/$O_2$ gas mixture (4%/400 cc/min initial dose, 1.5%/150 cc/min maintenance dose), which is delivered through a nose cone. The anesthetized animals are then placed in the RF coil with the animal handling system. An image intensity standard of 2% agar in 1 mM Gd-DTPA (Magnevist) may be placed beside the animal for data normalization.

In the exemplary embodiments described herein, the in vivo MRM is performed with a 9.4 T, 89 mm-bore system operating at a proton frequency of 400 MHz (Bruker Instruments, Billerica, Mass.). Constant body temperature of 37° C. is maintained using a thermocouple/heater system. A respiratory sensor can be placed on the abdomen of the animal for monitoring the depth and frequency of respiration. ECG monitoring will be performed using subcutaneous silver electrodes. The sensors are connected to the small animal monitoring unit.

After anatomical and angiographic MR localization, multi-contrast high-resolution images of the wall perpendicular and/or parallel to the entire arterial tree are obtained. MRM imaging is performed with the 2D and 3D high-resolution MR software and hardware methods described previously (Fayad ZA et al. Circulation. 1998; 98:1541-7; Choudhury RP et al. Atherosclerosis. 2002; 162:315-21; Choudhury RP et al. J Magn Reson Imaging. 2003; 17:184-189; Itskovich VV et al. Magn Reson Med. 2003; 49:381-5). Without removing the animal and the coil, the contrast agent was administered using the syringe pump at a constant rate of 50 ml/min. The procedure was followed with flush of saline.

Briefly, in order to characterize the plaque the following MRM is conducted (FIG. 4): 1) multicontrast blackblood pre-contrast enhanced (CE) MRM; and 2) post-contrast non-specific (Gd-DTPA) CE MR black-blood T1W imaging.

Histopathology, image and data analysis are performed to evaluate the MRM imaging with and without contrast-enhanced (Gd-DTPA) techniques. For histology processing, following MRM, randomly selected animals are sacrificed. The aorta from these animals is perfused, removed, and fixed (Rong et al., Circulation. 2001; 104:2447-52; Fayad et al., Circulation. 1998; 98:1541-7; Reis et al., J Vasc Surg. 2001; 34:541-7; Choudhury et al., Atherosclerosis. 2002; 162:315-21; Choudhury et al., J Magn Reson Imaging. 2003; 17:184-189; Itskovich et al., Magn Reson Med. 2003; 49:381-5; Itskovich et al., JMRI. 2003; Chereshnev et al., Journal of Surgical Research. 2003; 111:171-6, 2003). Serial sections of the aorta are cut at intervals matching corresponding MRM images. Co-registration is performed using external landmarks to the aorta, including arterial branches and the image processing algorithms explained above. Surrounding tissue is included in the sections for arterial support during fixation and to enhance co-registration through the use of fiducial markers as previously reported (Fayad et al., Circulation. 1998; 98:1541-7; Reis et al., J Vasc Surg. 2001; 34:541-7; Choudhury et al., Atherosclerosis. 2002; 162:315-21; Choudhury et al., J Magn Reson Imaging. 2003; 17:184-189; Itskovich et al., Magn Reson Med. 2003; 49:381-5; Itskovich et al., JMRI. 2003;in Press; Chereshnev et al., Journal of Surgical Research. 2003 111:171-6, 2003). The specimens are embedded in paraffin, and sections 5 µm thick are cut and stained with combined Masson's trichrome elastin (CME) stain and hematoxylin and eosin (H&E) stain. Other staining procedures also may be used.

Image analysis for plaque morphology (size, volume, etc.) and characterization may be performed by applying the cluster analysis, snake-based contour detection, and coregistration algorithms to both the MRM and histopathology images. The effectiveness of cluster and snake analyses as methods of automated atherosclerotic plaque component segmentation can be validated by comparing the registered color composite MRM images with the corresponding histopathology sections in both a qualitative and quantitative manner.

Qualitatively, the individual plaque components are identified on the cluster analyzed color composite matched MR images and histological slices for every specimen on the basis of signal intensity in the multicontrast MR images and histopathological staining. The color composite MR images and histopathological images are rated according to the histopathological classification from the Committee on Vascular Lesions of the Council of Atherosclerosis of the American Heart Association (AHA) (Fayad et al., Circulation. 1998; 98:1541-7; Fayad et al., Circulation. 2000; 101:2503-2509; Samber et al., Proc Intl Soc Mag Reson Med. 2003; In press; Stary et al., Circulation. 1995; 92:1355-74) which the inventors have previously used (Fayad et al., Circulation. 1998; 98:1541-7; Choudhury et al., Atherosclerosis. 2002; 162:315-21; Choudhury et al., J Magn Reson Imaging. 2003; 17:184-189; Helft et al., Circulation. 2002; 105:993-8; Fayad et al., Circulation. 2000; 101:2503-2509; Itskovich et al., JMRI. 2003; in Press).

Quantitatively, the digitized histopathological slices are subjected to the same cluster analysis procedure that the corresponding color composite MRM images were subjected to. The clustered histopathological images are characterized according to the AHA classification as above. Using the cluster and snake-based algorithms, the areas of these labeled regions are computed for both datasets as a percentage of total vessel wall area. The histopathological slices are matched to their corresponding MRM slices to allow for direct comparison of the labeled region areas. Additionally, The signal intensity of the vessel wall components and the adjacent muscle and the image intensity standard (to define the background MR signal) over time are determined by means of standard region-of-interest (ROI) measurements on the corresponding MRM images. An ROI placed outside the body, that contained no motion artifacts, will be selected to measure the standard deviation of the noise signal. Both normalized signal intensity (SI): $SI=SI_{plaque-post}/SI_{plaque-pre}$ and contrast-to-noise ratios (CNR): $CNR=SI_{plaque}-SI_{muscle}/SD_{noise}$ can be calculated.

For histopathological analysis of plaques, the components of the arterial wall and the atherosclerotic plaque can be determined by methods previously used by the inventors (Rong et al., Circulation. 2001; 104:2447-52; Fayad et al., Circulation. 1998; 98:1541-7). Three categories of plaque components may be correlated with the MRI images: 1) fibrous, 2) lipid, and 3) calcium. These categories are identified histopathologically by the following methods: intense green staining by CME (fibrous); foam cells and cholesterol clefts on H&E and CME (lipids); acellular purple crystals by H&E (calcium). In addition, immunohistochemical staining can be performed for α-actin (smooth-muscle cells), CD68 and MOMA2 (macrophages), the two principal cell types found in plaques.

After both MR images and histological sections are reviewed and categorized, comparison between the two sets of data can be performed. Given the difference in slice thickness between MRM histological cross-sections, three to four histological sections for each MR image location should be selected based on the relative distance of the MRM and histological sections from renal arteries and iliac bifurcation. In order to correct for shrinkage of the aortic specimen during histological processing, additional measures other than distance from the bifurcation for matching of the MRI and histological sections can be used. For example, the gross morphological features of the lumen and vessel wall, such as, the overall shape and size of the lumen and wall-may be compared. In addition, the location of large calcified regions, which appear hypointense on MRM, will aid in matching the cross-sections at each location. An agreement between MRI and histology may be defined as the presence of any plaque component region in the same quadrant on the MRI section and in all 3-4 of the matched histological sections. Pre- CE and post- MRM should be matched and registered.

Example 6

Use of Modified HDL as specific carrier for MR imaging of Atherosclerotic Plaques As discussed herein throughout, the ability to image the presence or biological activity of specific molecules in vivo (i.e., molecular imaging) in atherosclerotic plaques is of considerable interest. Current non-contrast and contrast-enhanced methods do not interrogate specific biochemical processes. In certain embodiments, the present invention is designed toe enhance distinctions among plaque components by the introduction of plaque-specific contrast agents that are related to molecular signatures involved in atherosclerosis. As discussed herein throughout, synthetic nanoparticles that mimic HDL are easily reconstituted, can carry a considerable contrast agent (i.e., Gd) payload, and are sufficiently small to penetrate readily in the extracellular space and freely enter and exist plaques. The present example describes methods and results of the use of nanoparticles containing a lipophilic gadolinium complex to create an MR contrast agent and the use of the nanoparticles as a diagnostic marker for atherosclerotic disease.

ApoAI/POPC/GdDTPADMPE/sodium cholate rHDL was prepared by spontaneous association of lipid-free apoAI and small unilamellar vesicles of POPC (palmitoyloleoyl phosphatidylcholine), and GdDTPEDMPE (dimiristoyl phosphatidylethanolamine). POPC (2.4 mg) and GdDTPADMPE (0.4 mg) in chloroform were dried in a thin film under nitrogen. Sodium cholate (3.1 mg) dissolved in TBS (200 μL) was added to the lipid film to give a turbid suspension that clearified after incubation at 37° C. for 1.5 hours. To the clear solution was added apoAI (1 mg) dissolved in 1 mL of TBS and the resulting mixture was allowed to incubate for one hour at 37° C. (Clay et al., Atherosclerosis, 2001, 157, 23) After incubation the sample was exhaustively dialyzed to get rid off the excess of cholate. The rHDL-GdDTPA-DMPE contrast agent diameter was determined with a laser light-scattering submicron particle sizer. Thirteen-month-old atherosclerotic Apolipoprotein E knockout (KO) mice (n=4) on a high fat diet and Wild Type (WT) (n=4) group underwent in vivo MR microscopy (MRM) of the abdominal aorta using a 9.4T MR system. Pre- and post- contrast enhanced (CE) (1 hour post) MRM was performed using a T1W black blood sequence. Sixteen contiguous 500 μm thick slices with an in-plane resolution of 93 μm were acquired in 30 minutes. The rHDL contrast agent (47.2 nmol) was injected via the tail vein. MRM images of the matched (pre and post) slices were used for analysis.

Figure 5:
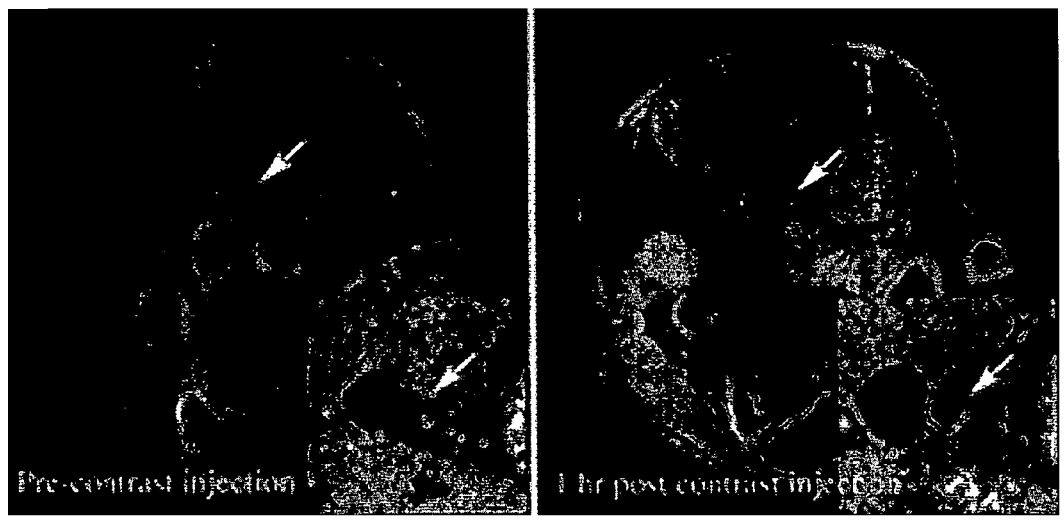
FIG. 5. Pre and post contrast (1 hour) injection of rHDL-GdDTPA-DMPE in an KO atherosclerotic mouse, showing the enhancement in the abdominal aorta (right; arrow).

The diameter of the rHDL contrast agent was 47 nm. The in vivo MR images reveal that after 1 hour post-injection of rHDL-GdDTPA-DMPE a substantial enhancement in the plaque in the abdominal aorta is observed. The ratio of the post to pre signal intensity of wall normalized with respect to muscle was 1.21 (21% enhancement) in KO mice after 1 hour (FIG. 5). There was no enhancement in the WT group.

These data demonstrate that in this in vivo MR study that Gd loaded nanoparticles localize and substantially enhance imaging of atherosclerotic plaques. Targeting molecules can be easily incorporated in the rHDL-GdDTPA-DMPE contrast agent. The targeting molecules will accomplish delivery and retention of the nanoparticles containing the contrast agent into plaques, based on the fairly extensive knowledge of specific molecules that are present in plaques at different stages of development. This may provide a way to achieve noninvasive optimal sensitive and specific in vivo molecular detection of atherosclerosis using MR.

Example 7

Discussion of Selection of Contrast Agents for MRI

The present example provides a general discussion of the use of metal agents currently in use in tissue imaging. As discussed herein above, contrast agents are used in various imaging modalities to enhance tissue contrast or to provide an indication of organ function or flow. One of the major differences between MRI and other imaging modalities is that in MRI the alterations in signal intensities of tissue depends on the effects of the contrast agents on the MR properties (i.e., water relaxation rates) rather than direct visualization of the contrast agent itself. Therefore, MRI contrast agents are imaged indirectly, by their effect on water relaxation rates. The present application focuses primarily on agents that are injected into the body and use chelated metals to change the water relaxation properties.

Many metal ions are good candidates as MR contrast agents. Paramagnetic contrast agents (atoms or molecules that have electrons in unpaired states) are the most commonly used today. Paramagnetic substances can influence relaxation rates in two distinctly different but related ways: 1) through alterations in the local magnetic fields by changing the local magnetic susceptibility; and 2) through an electron-nuclear dipolar interaction. The paramagnetic metal ion used in most current cardiovascular applications is gadolinium ($Gd^{3+}$) or Gd.

Metallic contrast agent properties are often discussed in terms of relaxivity. Since water is present at a very high concentration (55000 mM) and the contrast agent is typically at much lower concentration (0.1-1 mM) the contrast agent must act catalytically to relax the water protons to have a measurable effect. The relaxivities, $r_1$ and $r_2$, thus describes this catalytic efficiency.

In recent years, the Food and Drug Administration has approved a number of contrast agents for human use. The methods and compositions of the present invention may use any one or more of these approved metallic agents. These agents include:

| Generic Name | Product Name | Chemical Abbreviation | $r_1$, 0.5 T 37° C. | $r_2$, 0.5 T 37° C. | Osmolality[a] (osmol/kg) | Viscosity[a] (cP) |
|---|---|---|---|---|---|---|
| Gadopenetate | Magnevist Berlex, Schering | Gd-DTPA | 3.8 | | 1.96 | 2.9 |
| Gadoterate | Dotarem Guerbet | Gd-DOTA | 3.6 | 4.8 | 1.35 (4.02) | 2.0 (11.3) |
| Gadodiamide | Omniscan Nycomed | Gd-DTPA-BMA | 3.9 | | 0.79 (1.90) | 1.4 (3.9) |
| Gadoteridol | Prohance Bracco | Gd-HPDO3A | 3.7 | | 0.63 (1.91) | 1.3 (3.9) |
| Gadobutrol | Gadovist Schering | Gd-DO3A-butrol | 3.6 | | 0.57 (1.39) | 1.4 (3.7) |
| Gadoversetamide | Optimark Mallinckrodt | Gd-DTPA-BMEA | 4.7 | | 1.11 | 2.0 |
| Gadobenate | Multihance Bracco | Gd-BOPTA | 4.4 | 5.6 | 1.97 | 5.3 |
| Mangafodipir | Teslascan Nycomed | Mn-DPDP | 1.9 | 2.2 | 0.29 | 0.7 |

-continued

| Generic Name | Product Name | Chemical Abbreviation | $r_1$, 0.5 T 37° C. | $r_2$, 0.5 T 37° C. | Osmolality$^a$ (osmol/kg) | Viscosity$^a$ (cP) |
|---|---|---|---|---|---|---|
| Ferumoxide | Feridex IV Endorem Berlex; Guerbet | AMI-25 | 24 | 107 | 0.2 | 0.34 |
| Furucarbotran | Resovist Schering | SHU555a | 20 | 190 | 0.33 | 1.0 |

$^a$All concentrations 0.5M except those in parentheses, 1M, and Mn-DPDP (0.01M), AMI-25 (0.2M).

The majority of contrast agents used are gadolinium based. Other metals are capable of providing contrast, and iron and manganese have been used in commercially approved agents. In addition to the agents listed in the above table, other contrast agents that may be used include MS-325 (EPIX Medical Inc), B22956 (Bracca Diagnostics), both GD-based contrast agents that reversibly bind serum albumin. Blood pooling agents such as Gadomer-17 (Schering AG), and P792 (Laboratoire Guerbet). Iron oxide particles e.g., AMI-25, AMI-227 (Advanced Magnetics); NC100150 (Nycomed) also may be used in the applications described herein.

Gadolinium chelates are generally administered intravenously although some oral preparations have been described. Where intravenous administration is performed, it is often recommended that injection of Gd be followed by an injection of saline flush. The effective dose of Gd is approximately 0.1 mmol/kg of body weight (0.2cc/kg or 0.1 cc/lb). However, the FDA has approved gadoteridol fro triple dose injection volumes where an initial dose of 0.1 mmol/kg is followed by 0.2 mmol/kg upt to 30 minutes after the initial dose. Such FDA approved protocols may be used to provide general guidance as to amounts and regimens in which the synthetic nanoparticle compositions of the present invention should be administered to a subject for imaging purposes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the sarne or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A synthetic nanoparticle, said synthetic nanoparticle comprising: at least one apolipoprotein, said at least one apolipoprotein is not an apoB lipoprotein, at least one amphipathic lipid, and at least one metallic or non-metallic contrast agent linked through a chelator to a component of said nanoparticle, said at least one metallic or non-metallic contrast agent being present in an amount of between 5% to about 50% (w/w) of said nanoparticle, and said synthetic nanoparticle having a diameter of from about 5 nm to about 50 nm.

2. The synthetic nanoparticle of claim 1, wherein said nanoparticle is discoidal.

3. The synthetic nanoparticle of claim 1, wherein said nanoparticle is spherical.

4. The synthetic nanoparticle of claim 1, wherein said apolipoprotein is an amphipathic apolipoprotein or a fragment thereof.

5. The synthetic nanoparticle imaging agent of claim 1, wherein said metallic contrast agent is selected from the group consisting of Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), Er(III), Indium (In), Technetium (Tc), and Barium.

6. The synthetic nanoparticle of claim 1, wherein said non-metallic contrast agent is selected from the group consisting of Iodine (I), Bromine, Fluorescein, Carboxyfluorescein, and Calcein.

7. The synthetic nanoparticle of claim 1, wherein said metallic contrast agent is gadolinium.

8. The synthetic nanoparticle of claim 1, wherein said metallic contrast agent is conjugated to a lipid component of the synthetic nanoparticle.

9. The synthetic nanoparticle of claim 1, wherein said non-metallic contrast agent is conjugated to a lipid component of the synthetic nanoparticle.

10. The synthetic nanoparticle of claim 8, wherein said lipid component of the synthetic nanoparticle is selected from the group consisting of a sterol, a phospholipid, a sterol ester, a diacylglycerol and a triacylglycerol.

11. The synthetic nanoparticle of claim 10, wherein said phospholipid is selected from the group consisting of phosphatidylcholine (PC), phosphatidylethanolamine (PE), phosphatidylserine (PS), phosphatidylinositol (PI), phosphatidylglycerol (PG), cardiolipin (CL), a sphingolipid, sphingomyelin (SM), and phosphatidic acid (PA).

12. The synthetic nanoparticle of claim 11, wherein said phospholipid is PC.

13. The synthetic nanoparticle of claim 12, wherein said PC is POPC.

14. The synthetic nanoparticle of claim 11, wherein said phospholipid is PE.

15. The synthetic nanoparticle of claim 14, wherein said PE is poly-lysine PE.

16. The synthetic nanoparticle of claim 15, wherein said poly-lysine PE is poly-lysine dimyristoyl-PE (DMPE).

17. The synthetic nanoparticle of claim 10, wherein said sterol is cholesterol.

18. The synthetic nanoparticle of claim 10, wherein said sterol ester is cholesteryl ester.

19. The synthetic nanoparticle of claim 1, wherein said metallic contrast agent is conjugated to a protein component of the synthetic nanoparticle.

20. The synthetic nanoparticle of claim 1, wherein said non-metallic contrast agent is conjugated to a protein component of the synthetic nanoparticle.

21. The synthetic nanoparticle of claim 19 or claim 20, wherein said protein is selected from the group consisting of an apolipoprotein A-I, A-II, A-IV, C-I, C-II, C-III and E.

22. The synthetic nanoparticle of claim 1, comprising a phospholipids:steryl ester:sterol:TAG:ApoAI ratio (w/w) of 100:62:25:11:2.

23. The synthetic nanoparticle of claim 1, wherein said imaging agent comprises between 1 and 50 metallic contrast agent molecules per synthetic nanoparticle.

24. The synthetic nanoparticle of claim 1 or claim 23, wherein said metallic contrast agent molecule is conjugated to a phospholipid moiety and said phospholipid moiety accommodates more than one metallic agent molecule.

25. The synthetic nanoparticle of claim 1 or claim 23, wherein said non-metallic contrast agent molecule is conjugated to a phospholipid moiety and said phospholipid moiety accommodates more than one metallic agent molecule.

26. The synthetic nanoparticle of claim 1, wherein said synthetic nanoparticle comprises 10 metallic contrast agent molecules per synthetic nanoparticle.

27. The synthetic nanoparticle of claim 1, wherein said synthetic nanoparticle comprises between about 5 mg and about 30 mg of apolipoprotein.

28. The synthetic nanoparticle of claim 1, wherein said synthetic nanoparticle comprises between about 80 and about 90 phospholipids per synthetic nanoparticle.

29. The synthetic nanoparticle of claim 1, wherein said synthetic nanoparticle comprises about 2 apolipoprotein molecules per synthetic nanoparticle.

30. The synthetic nanoparticle of claim 1, wherein said synthetic nanoparticle comprises about 1 apolipoprotein molecule to about 40 phospholipid molecules.

31. The synthetic nanoparticle of claim 1, wherein said agent further comprises a targeting moiety.

32. The synthetic nanoparticle of claim 31, wherein said targeting moiety is selected from the group consisting of an antibody, a receptor, a ligand, a peptidomimetic agent, an aptamer and a product of phage display.

33. The synthetic nanoparticle of claim 31, wherein said targeting moiety is conjugated to a detectable label.

34. The synthetic nanoparticle of claim 31, wherein said imaging agent has a diameter of between about 5 to about 18 nm.

35. The synthetic nanoparticle of claim 31, wherein said imaging agent has a diameter of between about 5 to about 12 nm.

36. The synthetic nanoparticle of claim 31, wherein said imaging agent has a diameter of less than 10 nm.

37. The synthetic nanoparticle of claim 1, wherein said imaging agent comprises two or more different metallic contrast agents.

38. The synthetic nanoparticle of claim 1, wherein said imaging agent comprises two or more different non-metallic contrast agents.

39. The synthetic nanoparticle of claim 31, further comprising a drug.

40. The synthetic nanoparticle of claim 1, wherein said synthetic nanoparticle is non-inflammatory.

41. A pharmaceutical composition comprising said synthetic nanoparticle of claim 1 and a pharmaceutically acceptable carrier or diluent.

42. A method of in vivo imaging of a site within a subject comprising administering to said subject said synthetic nanoparticle of claim 1 comprising a metallic or non-metallic contrast agent conjugated to a component of said synthetic nanoparticle.

43. The method of claim 42, wherein said synthetic nanoparticle comprises a targeting moiety that specifically targets said synthetic nanoparticle to said in vivo site.

44. The method of claim 42, wherein said in vivo site is the site of an atherosclerotic plaque.

45. The method of claim 44, wherein said targeting moiety is selected from the group consisting of antibodies against lipoprotein lipase, oxidized epitopes on atherosclerotic plaques oxLDL MDA, antibodies against matrix metalloproteinases and anti-tissue factor antibodies.

46. The method of claim 44, wherein said in vivo site is the site of a tumor and said targeting moiety comprises a moiety that recognizes a tumor-specific binding partner present on said tumor.

47. The method of claim 46, wherein said binding partner is selected from the group consisting of an antibody against a tumor-specific antigen, a receptor for a ligand expressed by said tumor cell, and a ligand for a receptor expressed by said tumor.

48. The method of claim 44, wherein said in vivo site is the site of an organ and said targeting moiety recognizes a target that is exclusively expressed on said organ.

49. The method of claim 44, wherein said in vivo site is the site of platelet deposition in an animal and said targeting moiety comprises a fibronectin II/bIIIa receptor ligand or a fibrin binding protein.

50. A synthetic nanoparticle, said synthetic nanoparticle comprising: at least one apolipoprotein that is not an apoB lipoprotein, at least one amphipathic lipid, and at least one metallic or non-metallic contrast agent sequestered in the core of said synthetic nanoparticle.

51. The synthetic nanoparticle of claim 50, wherein said one metallic or non-metallic contrast agent is present in an amount of between 5% to about 50% (w/w) of said nanoparticle.

52. The synthetic nanoparticle of claim 50, wherein said synthetic nanoparticle has a diameter of from about 5 nm to about 50 nm.

53. The synthetic nanoparticle of claim 50, wherein the contrast agent is a metallic crystal or particulate.

54. The synthetic nanoparticle of claim 53, wherein the contrast agent is a metal oxide or a quantum dot.

55. The synthetic nanoparticle of claim 50, further comprising a second metallic or non-metallic contrast agent linked through a chelator to a component of said nanoparticle.

56. The synthetic nanoparticle of claim 55, wherein said first and second contrast agents are different agents.

57. A pharmaceutical composition comprising the synthetic nanoparticle of claim 50 and a pharmaceutically acceptable carrier or diluent.

58. A method of in vivo imaging a site within a subject comprising administering to said subject the pharmaceutical composition of claim 57 and imaging a site of said subject.

* * * * *

UNITED STATES PATENT AND TRADEMARK OFFICE
CERTIFICATE OF CORRECTION

PATENT NO. : 8,097,283 B2
APPLICATION NO. : 10/557094
DATED : January 17, 2012
INVENTOR(S) : Fisher et al.

Page 1 of 1

It is certified that error appears in the above-identified patent and that said Letters Patent is hereby corrected as shown below:

On the Title Page, in item (75), under "Inventors", in Column 1, Line 3, delete "Winnewood," and insert -- Wynnewood, --, therefor.

In the Claims:

In Column 38, Line 21, in Claim 5, delete "imaging agent of" and insert -- of --, therefor.

Signed and Sealed this
Fourteenth Day of October, 2014

Michelle K. Lee
*Deputy Director of the United States Patent and Trademark Office*